US00RE41028E

(19) United States
(12) Reissued Patent
Podolsky

(10) Patent Number: US RE41,028 E
(45) Date of Reissued Patent: Dec. 1, 2009

(54) TREATING EYE DISORDERS INTESTINAL TREFOIL PROTEINS

(75) Inventor: Daniel K. Podolsky, Wellesley, MA (US)

(73) Assignee: The General Hospital Corporation, Boston, MA (US)

(21) Appl. No.: 10/457,157

(22) Filed: Jun. 9, 2003

Related U.S. Patent Documents

Reissue of:
(64) Patent No.: 6,525,018
Issued: Feb. 25, 2003
Appl. No.: 09/313,434
Filed: May 17, 1999

U.S. Applications:

(63) Continuation-in-part of application No. 10/362,310, filed as application No. PCT/US97/06004 on Apr. 11, 1997, which is a continuation-in-part of application No. 08/631,469, filed on Apr. 12, 1996, now Pat. No. 6,221,840.

(51) Int. Cl.
*A01N 37/18* (2006.01)
*A61K 38/00* (2006.01)

(52) U.S. Cl. ..... 514/2
(58) Field of Classification Search ..... 530/300; 514/2
See application file for complete search history.

(56) References Cited

U.S. PATENT DOCUMENTS

| | | | |
|---|---|---|---|
| 4,370,317 | A | 1/1983 | Jorgensen et al. |
| 5,541,210 | A | 7/1996 | Cupps et al. |
| 5,703,047 | A | 12/1997 | Wilson |
| 5,783,416 | A | 7/1998 | Thim et al. |
| 5,830,706 | A | 11/1998 | Mascarenhas et al. |
| 5,843,701 | A | 12/1998 | Gold et al. |
| 6,063,755 | A | 5/2000 | Podolsky |
| 6,221,840 | B1 | 4/2001 | Podolsky |
| 6,288,118 | B1 | 9/2001 | Nieman et al. |
| 6,316,218 | B1 | 11/2001 | Podolsky |
| 6,426,404 | B1 | 7/2002 | Podolsky |
| 6,525,018 | B1 | 2/2003 | Podolsky |
| 6,685,917 | B2 | 2/2004 | Rosenthal et al. |
| 6,984,628 | B2 | 1/2006 | Bakhit et al. |
| 2002/0052483 | A1 | 5/2002 | Podolsky |
| 2002/0119104 | A1 | 8/2002 | Rosenthal et al. |
| 2002/0151472 | A1 | 10/2002 | Thim et al. |
| 2002/0187487 | A1 | 12/2002 | Goldenring et al. |
| 2003/0032585 | A1 | 2/2003 | Thim et al. |
| 2003/0077696 | A1 | 4/2003 | Thim et al. |
| 2003/0078205 | A1 | 4/2003 | Podolsky |
| 2003/0105016 | A1 | 6/2003 | Podolsky |
| 2003/0114384 | A1 | 6/2003 | Podolsky |
| 2003/0134797 | A1 | 7/2003 | Podolsky |
| 2003/0148949 | A1 | 8/2003 | Podolsky |
| 2003/0153496 | A1 | 8/2003 | Thim et al. |
| 2003/0166535 | A1 | 9/2003 | Podolsky |
| 2003/0181383 | A1 | 9/2003 | Podolsky |
| 2003/0181384 | A1 | 9/2003 | Podolsky |
| 2003/0185838 | A1 | 10/2003 | Podolsky |
| 2003/0185839 | A1 | 10/2003 | Podolsky |
| 2003/0186880 | A1 | 10/2003 | Podolsky |
| 2003/0186882 | A1 | 10/2003 | Podolsky |
| 2003/0186886 | A1 | 10/2003 | Podolsky |
| 2003/0215431 | A1 | 11/2003 | Thim et al. |
| 2003/0225250 | A1 | 12/2003 | Podolsky |
| 2004/0171544 | A1 | 9/2004 | Barker et al. |
| 2005/0287640 | A1 | 12/2005 | Thim et al. |
| 2006/0019881 | A1 | 1/2006 | Thim et al. |
| 2006/0046958 | A1 | 3/2006 | Bakhit et al. |
| 2006/0111278 | A1 | 5/2006 | Thim et al. |
| 2006/0188471 | A1 | 8/2006 | Podolsky |
| 2006/0189526 | A1 | 8/2006 | Podolsky |
| 2006/0211605 | A1 | 9/2006 | Thimm et al. |
| 2006/0241037 | A1 | 10/2006 | Olejnik et al. |
| 2006/0293221 | A1 | 12/2006 | Thim et al. |
| 2007/0062517 | A1 | 5/2007 | Barker |
| 2007/0148733 | A1 | 7/2007 | Woon et al. |

FOREIGN PATENT DOCUMENTS

| | | |
|---|---|---|
| EP | 0 534 310 | 3/1993 |
| FR | 2769502 | 4/1999 |
| WO | WO 86/02271 | 4/1986 |
| WO | WO 92/14837 | 9/1992 |
| WO | WO 94/17102 | 8/1994 |
| WO | WO 96/06861 | 3/1996 |
| WO | WO 97/38712 | 10/1997 |
| WO | WO 98/30592 | 7/1998 |
| WO | WO 99/18927 | 4/1999 |
| WO | WO 00/20868 | 4/2000 |
| WO | WO 00/074655 | 12/2000 |
| WO | WO 01/02570 | 1/2001 |
| WO | WO 01/29269 | 4/2001 |
| WO | WO 02/46226 | 6/2002 |
| WO | WO 02/085402 | 10/2002 |
| WO | WO 02/102399 | 12/2002 |
| WO | WO 02/102403 | 12/2002 |
| WO | WO 03/068817 | 8/2003 |
| WO | WO 2004/064860 A1 | 8/2004 |
| WO | WO 2005/009459 A1 | 2/2005 |
| WO | WO 2005/039619 A1 | 5/2005 |
| WO | WO 2005/039640 A1 | 5/2005 |

OTHER PUBLICATIONS

Richter et al, J. Biol. Chem. 270(4):1612–1616, 1995.*
Harmer et al, Biochemistry, 43(3):629–640, 2004.*
Bare et al, Biochemical and Biophysical Research Communications, 205(1):877–879, 1994.*
Wbsters Dictionary—definition trefoil, 1998.*
MSN Encarta Dictionary—definition for trefoil, 2006.*
Blast alignment of human and rat ITF, currently know as Trefoil factor 3 (TTF3), 2 pages, 2007.*

(Continued)

*Primary Examiner*—Patricia A Duffy
(74) *Attorney, Agent, or Firm*—Clark & Elbing LLP

(57) ABSTRACT

Intestinal trefoil factors and nucleic acids encoding intestinal trefoil factors are disclosed. The intestinal trefoil factors disclosed are resistant to destruction in the digestive tract and can be used for the treatment of peptic ulcer diseases, inflammatory bowel diseases, eye disorders and other insults.

14 Claims, 12 Drawing Sheets

OTHER PUBLICATIONS

Alderman et al., "Insights into the mechanisms of gastric adaption to aspirin–induced injury: A role for regenerating protein but not trefoil peptides," *Laboratory Investigation* 83:1415–1425 (2003).
Hanby et al., "Expression of the trefoil peptides pS2 and human spasmolytic polypeptide (hsp) in barrett's metaplasia and the native esophageal epithelium: delineation of epithelial phenotype," *J. of Pathology* 173:213–219 (1994).
Hauser et al., "hP1.B5 A human P–domain peptide homologous with rat intestinal trefoil factor, is expressed also in the ulcer–associated cell lineage and the uterus," *Proc. Natl. Acad. Sci.*90:6961–6965 (1993).
Hawkey et al., "Gastrointestinal safety of AZD3582, a cyclooxygenase inhibiting nitric oxide donator: proof of concept study in humans," *Gut* 52:1537–1542 (2003).
Muskett et al., "Solution structure of the disulfide–linked dimer of human intestinal trefoil factor (TFF3): The intermolecular orientation and interactions are markedly different from those of other dimeric trefoil proteins," *Biochemistry* 42:15139–15147 (2003).
Poulsom et al., "Trefoil peptides: a newly recognized family of epithelial mucin–associated molecules," *Am. J. Physiol.* 265:G205–213 (1993).
Thim, "Trefoil peptides: A new family of gastrointestinal molecules," Digestion 55:353–360 (1994).
Van de Bovenkamp et al, "Gastric–type mucin and TFF–peptide expression in Barrett's oesophagus is disturbed during increased expression of MUC2," *Histopathology* 42:555–565 (2003).
Williams et al., "pS2 transfection of murine adenocarcinoma cell line 410.4 enhances dispersed growth pattern in a 3–D collagen gel," *J. Cell Sci.* 109:63–71 (1996).
Zhang, "The therapeutic effect of recombinant human trefoil factor 3 on hypoxia–induced necrotizing enterocolitis in immature rat," *Regulatory Peptides* 116:53–60 (2003).
Attwood et al., *Science* 290:471–473 (2000).
Babyatsky et al., "Trefoil peptides protect against ethanol and indomethacin induced gastric injury in rats" *Gastroenterology* 106: A43 (1994).
Burling et al., *American Journal of Veterinary Research* 61:1150–1155 (2000).
Dignass et al., "Trefoil peptides promote epithelial migration through a transforming growth factor β–independent pathway" *J. Clin. Invest.* 94:376–383 (1994).
Falk et al., "Expression of a human α–1/,3/4–Fucosyltransferase in the pit cell linease of FVB/N mouse stomach results in production of $Le^b$–containing glycoconjugates: a potential transgenic mouse model for studying He licobacter pylori infection" *Proc. Natl. Sci. USA* 92:1515–1519 (1995).
Gerhold et al., *BioEssays* 18:973–981 (1996).
Jakowlew et al., "Sequence of the pS2 mRNA induced by estrogen in the human breast cell line MCF–7" *Nucleic Acid Res* .12:2861–2878 (1994).
Jeffrey et al., "Spasmolytic–polypeptide: A trefoil peptide secreted by rat gastric mucous cells" *Gastroenterology* 106:336–345 (1994).
Jorgensen et al., "Pancreatic spasmolytic polypeptide (PSP): III. Pharmacology of a new porcine pancreatic polypeptide with spasmolytic and gastric acid secretion inhibitory effects" *Regulatory Peptides* 3:231–243 (1982).
Modlin et al., "Trefoil peptides: mitogens, motogens, or mirages?" *J. Clin. Gastroenterol.* 25(Supp. 1): S94–S100 (1997).
Mori et al., "Identification of a polypeptide secreted by human breast cancer cells (MCF–7) as the human estrogen–responsive gene (pS2) product" *Biochem. Biophys. Res. Comm.* 155:366 (1988).
Okayasu et al., "A novel method in the induction of reliable experimental acute and chronic ulcerative colitis in mice" *Gastroenterology* 98:694–702 (1990).
Podolsky et al., "Demonstration of distinct subpopulations defined by mucin–specific monoclonal antibodies" *J. Clin. Invest.* 77:1263–1271 (1986).
Podolsky et al., "Identification of human intestinal trefoil factor" *J. Biol. Chem.* 268:6698–6702 (1993).
Podolsky et al., "Latent transformed growth–inhibiting factor in human malignant effusions", *Cancer Res.* 48:418–424 (1988).
Russell et al., *J. Mol. Biol.* 244:332–350 (1994).
Sands et al., "The trefoil peptide family" *Ann. Rev. of Physiol.* 58:253–273 (1996).
Suemori et al., "Identification and characterization of rat intestinal trefoil factor: Tissue and cell–specific member of the trefoil protein family" *Proc. Natl. Acad. Sci. USA* 88:11017–11021 (1991).
Thim et al., "The amino acid sequence of pancreatic spasmolytic polypeptide" *Biochem. Biophys. Acta.* 827:410–418 (1985).
Wells et al., *J. of Leukocyte Biol.* 61:545–555 (1997).
U.S. Appl. No. 07/655,965, filed Feb. 14, 1991, Podolsky.
U.S. Appl. No. 07/837,192, filed Feb. 13, 1992, Podolsky.
U.S. Appl. No. 10/362,310, filed Feb. 19, 2003, Podolsky.
Amorium et al., "Microparticles for delivering therapeutic peptides and proteins to the lumen of the small intestine," *Eur J Pharm Biopharm.* 52:39–44 (2001).
Babyatsky et al., "Oral trefoil peptides protect against ethanol and indomethacin–induced gastric injury in rats," *Gastroenterology* 110:489–497 (1996).
Beck et al., "Growth factors in inflammatory bowel disease," *Inflam Bowel Dis.* 5(1):44–60 (1999).
Beers, The Merck manual of diagnostic and therapy, seventh edition, pp. 556–568, 1044–1047, 1050, and 1110–1113 (1999).
Bork et al., "Powers and pitfalls in sequence analysis: the 70% hurdle," *Genome Res.* 10:398–400 (2000).
Bork et al., "Go hunting in sequence databases but watch out for the traps," *Trends Genet.* 12(10):425–427 (1996).
Botoman et al., "Management of inflammatory bowel disease," *Am Fam Physican.*57:57–68 (1998).
Brenner, "Errors in genome annotation," *Trends Gent.* 15(4):132–133 (1999).
Burgess et al., "Possible dissociation of the heparin–binding and mitogenic activities of heparin–binding (acidic fibroblast) growth factor–1 from its receptor–binding activities by site–directed mutagenesis of a single lysine residue," *J Cell Biol.* 111:2129–2138 (1990).
Byrne et al., "rHuKGF ameliorates symptoms in DDS and CD4*CD45RB$^{RI}$T cell transfer mouse models of inflammatory bowel disease," *Am J Physiol Gastrointest Liver Physiol.* 282:G690–G701 (2002).
Chinery et al., "Combined intestinal trefoil factor and epidermal growth factor is prophylactic against indomethacin–induced gastric damage in rat," *Clin Sci* (*Lond*). 88:401–403 (1995).
Cook et al., "Oral human spasmolytic polypeptide protects against aspirin–induced gastric injury in rats," *J Gastroenterol Hepatol.* 13:363–370 (1998).

Doerks et al., "Protein annotation: detective work for function prediction," *Trends Genet.* 14(6):248–250 (1998).

Dorland's medical dictionary—definition of mucositis, Dec. 16, 1997.

Fleiszig et al., "Relationship between cytotoxicity and corneal epithelial cell invasion by clinical isolates of *Pseudomones aeruginosa," Infect Immun.* 64(6): 2288–2294 (1996).

Frandsen et al., "Receptor binding of pancreatic spasmolytic polypeptide (PSP) in rat intestinal mucosal cell membranes inhibits the adenylate cyclase activity," *Regul Pept.* 16:291–297 (1986).

Graness et al., "Protein kinase C and ERK activation are required for TFF–peptide–stimulated bronchial epithelial cell migration and tumor necrosis factor–alpha–induced interleukin–6 (IL–6) and IL–8 secretion," J Biol Chem. 277:18440–18446 (2002).

Hammer, "Was gibt es neues in der diagnostik und therapie des morbus crohn und der colitis ulcerosa," *Gasteroenterologische Abteilung, Kantonsspital St. Gallen.* 124:452–460 (1994). (Abstract in English).

Hoffmann et al., "Molecular medicine of TFF–peptides: From gut to brain," *Histology and Histropathology* 16:319–334 (2001).

http://allaboutvision.com/conditions:cataracts.

http://allaboutvision.com/conditions:diabetic retinopathy.

http://allaboutvision.com/conditions:dry eye syndrome.

http://allaboutvision.com/conditions:glaucoma.

http://allaboutvision.com/conditions:hyperopia.

http://allaboutvision.com/conditions:macular degeneration.

http://medterms.com,definition of mucositis.

http://www.mic.ki.se/Diseases:eye/C11.html.

Itoh et al., "A paradoxical reduction in susceptibility to colonic injury upon targeted transgenic ablation of goblet cells," *J Clin Invest.* 104(11):1539–1547 (1999).

Itoh et al., "Goblet–cell–specific transcription of mouse intestinal trefoil factor gene results from collaboration of complex series of positive and negative regulatory elements," *Biochem J.* 341:461–472 (1999).

Iwakiri et al., "A silencer inhibitor confers specific expression of intestinal trefoil factor in gobletlike cell lines," *Am J Physiol Gastrointest Liver Physiol.* 280:G1114–G1123 (2001).

Iwakiri et al., "Keratinocyte growth factor promotes goblet cell differentiation through regulation of goblet cell silence inhibitor," *Gasterology* 120:1372–1380 (2001).

Juhász et al., "Repopulation of langerhans cells during wound healing in an experimental human skin/SCID mouse model," *Immunol Lett.* 52:125–128 (1996).

Kanai et al., "Intestinal trefoil factor induces inactivation of extracellular signal–regulated protein kinase in intestinal epithelial cells," *Proc Natl.Acad Sci U S A*95:178–182 (1998).

Kannan et al., "Human pS2/trefoil factor 1: production and characterization in pichia pastoris," *Protein Expr Purif.* 21:92–98 (2001).

Kato et al., "Effects of growth factors and trefoil peptides on migration and replication in primary oxyntic cultures," *Am J Physiol.* 276(5): G1105–G1116 (1999).

Kindon et al., "Trefoil peptide protection of intestinal epithelial barrier function: cooperative interaction with mucin glycoprotein," *Gastroenterology* 109:516–523 (1995).

Kinoshita et al., "Distinct pathways of cell migration and antiapoptotic response to epithelial injury: structure–function analysis of human intestinal trefoil factor," *Mol Cell Bio.* 20(13):4680–4690 (2000).

Kjellev et al., "Effect of systemically administered TFF3 on murine experimental colitis," *IV TFF Conference*, Strasbourg, France (Abstract/Poster) (Dec. 2–4, 2004).

Lazer et al., "Transforming growth factor alpha: mutation of aspartic acid 47 and leucine 48 results in different biological activities," *Mol Cell Bio.* 8(3): 1247–1252 (1988).

Lefebvre et al., "The mouse one P–Domain (pS2) and two P–Domain (mSP) genes exhibit distinct patterns of expression," *J Cell Biol.* 122:191–198 (1993).

Lemercinier et al., "High–resolution solution structure of human intestinal trefoil factor and functional insights from detailed structural comparisons with the other members of the trefoil family of mammalian cell motility factors," *Biochemistry* 40:9552–9559 (2001).

Life Sciences Dictionary; definition of lesion, 1998.

Mashimo et al. "Impaired defense of intestinal mucosa in mice lacking intestinal trefoil factor," *Science* 274:262–265 (1996).

Mason et al., "Functional analysis of the cysterine residues of activin A," *Mol Endocrinol.* 8(3):325–332 (1994).

May et al., "The closely related estrogen–regulated trefoil proteins TFF1 and TFF3 have markedly different hydrodynamic properties, overall charge, and distribution of surface charge," *Biochemistry* 42:8250–8259 (2003).

McKenzie et al., "Topical and intravenous administration of trefoil factors protect the gastric mucosa from ethanol–induced injury in the rat," *Aliment Pharmacol Ther.* 14:1033–1040 (2000).

Moss and Wright, "Molecular aspects of mucosal repair: a summary," *Yale Journal of Biology and Medicine* 69(2): 155–158 (1996).

National Cancer Institute; dictionary of cancer terms—definition of lesion, 1998.

Ngo et al., "Computational complexity, protein structure prediction, and the Levinthal paradox," *The Protein Folding Problem and Tertlary Structure Prediction* K. Merz and S. Le Grand, Editors 492–495 (1994).

Nikolaidis et al., "Trefoil factor–2 is an allergen–induced gene regulated by Th2 cytokines and STAT6 in the lung," *Am J Resp Cell Mol Biol.* 29:458–464 (2003).

Oertel et al., "Trefoil factor family—peptides promote migration of human bronchial epithelial cells," *Am J Respi. Cell Mol Biol.* 25:418–424 (2001).

Ogata et al., "Identification of a goblet–cell–specific enhancer element in the rat intestinal trefoil factor gene promoter bound by a goblet cell nuclear protein," *J Biol Chem.* 273(5):3060–3067 (1998).

Ogata et al., "Trefoil peptide expression and secretion is regulated by neuropeptides and acetylcholine," *Am J Physiol* 273(2 Pt 1):G348–G354 (1997).

On–Line Medical Dictionary; definition of cervix uteri—synonym is cervix, Mar. 5, 2000.

On–Line Medical Dictionary; definition of mucostis, Dec. 16, 1997.

Paulsen et al., "TFF peptides in the human efferent tear ducts," *Invest Ophthalmol Vis Sci.* 43:3359–3364 (2002).

Playford, "Trefoil peptides: what are they and what do they do?", *J R Coll Physicians Lond.* 31(1):37–41 (1997).

Poulsen et al., "Injected TFF1 and TFF3 bind to TFF2–immunoreactive cells in the gastrointestinal tract in rats," *Req Peptides* 115:91–99 (2003).
Poulsen et al., "Metabolism of oral trefoil factor 2 (TFF2) and the effect of oral and parenteral TFF2 on gastric and duodenal ulcer healing in the rat," *Gut* 45:516–522 (1999).
Rio et al., "Breast–cancer–associated pS2 protein: Synthesis and secretion by normal stomach mucosa," *Science* 241:705–708 (1988).
Rudinger, "Characteristics of the amino acids as components of a peptide hormone sequence" Peptide Hormones J.A. Parsons,University Park Press, Baltimore pp. 1–7 (1976).
Sands et al., "Molecular cloning of the rat intestinal trefoil factor gene, characterization of an intestinal goblet cell–associated promoter," *J Biol Chem.*270(16):9353–9361 (1995).
Segars et al., "Mesalamine and olsalazine:5–aminosalicytic acid agents for the treatment of inflammatory bowel disease," *Clin Pharm.*11:514–528 (1992).
Silva et al., "Trefoil factor family domain peptides in the human respiratory tract," *Journal of Pathology* 190:133–142 (2000).
Skolnick et al., "From genes to protein structure and function: novel applications of computational approaches in the genomic era," *Trends Biotechnol.*18(1): 34–39 (2000).
Smith et al., The challenges of genome sequence annotation or "the devil is in the details", *Nature Biotechnol.*15:1222–1223 (1997).
Stein et asl., "Comparative tolerability for inflammatory bowel disease," *Drug Saf.*23: 429–448 (2000).
Taupin et al., "Intestinal trefoil factor confers colonic epithelial resistance to apoptosis," *Proc Nat Acad Sci* 97(2):799–804 (2000).
Taupin et al., "Mitogen–activated protein kinase regulates intestinal epithelial differentation," *Gastroenterology* 116:1072–1080 (1999).
Tebbutt et al., "Reciprocal regulation of gastrointestinal homostatis by SHP2 and STAT–mediated trefoil gene activation in gp130 mutant mice," *Nat Med* 8:1089–1097 (2002).
Tesfaigzi, "Processes involved in the repair of injured airway epithelia," *Arch Immunol Ther Exp.*51:283–288 (2003).
Thim et al., "Characterization of human and rat intestinal trefoil factor produced in yeast," *Biochemistry* 34:4757–4764 (1995).
Thim et al., "Pancreatic spasmolytic polypeptide (PSP):II. Radioimmunological determination of PSP in porcine tissues, Plasma and pancreatic juice," *Regul Pept.*3:221–230 (1982).
Tran et al., "Trefoil peptide TFF2 (spasmolytic polypeptide) potently accelerates healing and reduces inflammation in a rat model of colitis," *Gut*44:636–642 (1999).
Wang et al., "Effect of antibody against integrin α4 on bleomycin–induced pulmonary fibrosis in mice," *Biochem Pharmacol.*60:1949–1958 (2000).
Wang et al., "Inflammation intersection: gp130 balances gut irritation and stomach cancer," *Nat Med.*8:1080–1082 (2002).
Wiede et al., "Synthesis and localization of the mucin–associated TFF–peptides in the human uterus," *Cell Tissue Res.*303:109–115 (2001).
Xian et al., "Temporal changes in TFF3 expression and jejunal morphology during methotrexate–induced damage and repair,"*Am J Physiol.*277 (Gastrointest. Liver Physiol. 40): G785–G795 (1999).
Yoo et al., "Cytokinese in restitution; gastrointestinal mucosal repair and experimental therapeutics," Front Gastrointest. Res. Basel. Karger 25:14–28 (2002).
Communication and Supplementary European Search Report mailed Apr. 4, 2005 (EP 02 75 7620).
Communication and Supplementary Eurpoean Search Report mailed Apr. 15, 2005 (EP 02 80 0937).
Communication and Supplementary European Search Report mailed Jan. 25, 2005 (EP 02 78 6828).
Communication and Supplementary European Search Report mailed Jul. 5, 2004 (EP 97 92 1148).
Communication and Supplementary European Search Report mailed Jun. 1, 2004 (EP 02 76 4324).
International Search Report mailed Jul. 24, 1997 (PCT/US97/06004).
International Search Report mailed Mar. 28, 2003 (PCT/US02/31998).
International Search Report mailed May 27, 2003 (PCT/US02/38258).
International Search Report mailed Oct. 20, 2003 (PCT/US03/09195).
International Search Report mailed Oct. 8, 2004 (PCT/US02/28339).
International Search Report mailed Sep. 11, 2002 (PCT/US02/12891).
International Search Report mailed Aug. 31, 2006 (PCT/US03/34796).
U.S. Appl. No. 11/821,367 filed Jun. 21, 2007, Podolsky.
Communication and Search Results from European Patent Office, mailed May 16, 2006 (EP 97921148.9).
Cuzzocrea et al., "Celecoxib, a selective cyclo–oxygenase–2 inhibitor reduces the severity of experimental colitis induced by dintrobenzene sulfonic acid in rats," *Eur. J. Pharmacol.*431:91–102 (2001).
David et al., "Corneal wound healing modulation using basic fibroblast growth factor after excimer laser photoefractive keratecomy," *Cornea*14:227–234 (1995).
Göke et al., "Trefoil peptides promote restitution of wounded corneal epithelial cells," *Exp. Cell Res.*264:337–344 (2001).
Harlow and Lane, "Antibodies: a laboratory manual," *Cold Spring Harbor Press Inc.*, 72–73 (1988).
Harlow and Lane, "Antibodies: a laboratory manual," *Cold Spring Harbor Press Inc.*, p. 76 (1988).
Hauser et al., "xP2, a New Member of the P–Domain Family of Potential Growth Factor Members, is Synthesized in *Xenopus laevis* Skin," *J. Biol. Chem.*267(20):14451–14455 (1992).
http://www.medterms.com; definition of gastrointestinal tract Jan. 12, 1998.
http://cancerweb.ncl.ac.uk; definition of gastrointestinal tract, Feb. 5, 2007.
http://cancerweb.ncl.ac.uk; definition of trefoil, Mar. 1, 1998.
http://www.thedoctorsdoctor.com; definition and description of gastrointestinal system, Jun. 28, 2002.
http://www.hon.ch; definition of gastrointestinal system, Feb. 2, 2007.
Jagla et al., "Localization of TFF3 peptide to porcine conjunctival goblet cells," *Cell Tissue Res.*296:525–530.
Jorgensen et al., "Pancreatic spasmolytic polypeptide (PSP): I. Preparation and initial chemical characterization of a new polypeptide from porcine pancreas," *Regul. Pept.*3:207–219 (1982).

Kalin and Bjorkholm, "Prophylactic and empirical treatment of mycoses in neutropenic fever," *Lakartidningen* 98(16):1899–1903 (2001), abstract only.
Khan–Lim et al., "Trefoil factors in normal and dry eyes," *Trefoils & Mucins 2002*, Keble College, Oxford, U.K., Apr. 2–4, 2002 (abstract).
Murali et al., "Effect of topically administered platelet–derived growth factor on corneal wound strength," *Curr. Eye Res.*13:857–862 (1994).
Paulsen et al., "Distribution of TFF–peptides and mucins in human nasolacrimal ducts," *Trefoils & Mucins 2002*, Keble College, Oxford, U.K., Apr. 2–4, 2002 (abstract).
Paulsen et al., "Distribution of mucins in human pterygia," *Trefoils & Mucins 2002*, Keble College, Oxford, U.K., Apr. 2–4, 2002 (abstract).
Poulsen et al., "Luminal and parental TFF2 and TFF3 dimer and monomer in two models of experimental colitis in the rat," *Regulatory Peptides* 126:163–171 (2005).
Smith et al., "Production of human beta interferon in insect cells infected with a baculoviris expression vector," *Mol. Cell. Biol.*3:2156–2165 (1983).
Tomasetto et al., "hSP, the domain–duplicated homolog of pS2 protein, is co–expressed with pS2 in stomach but not in breast carcinoma," *EMBO J.*9:407–414 (1990).
Office Action for U.S. Appl. No. 10/434,752 (mailed Oct. 1, 2004).
Office Action for U.S. Appl. No. 10/434,752 (mailed Feb. 15, 2006).
Office Action for U.S. Appl. No. 10/434,752 (mailed Jun. 1, 2007).
Office Action for U.S. Appl. No. 10/266,069 (mailed Feb. 27, 2007).
Office Action for U.S. Appl. No. 10/434,636 (mailed Sep. 30, 2004).
Office Action for U.S. Appl. No. 10/434,636 (mailed Feb. 14, 2006).
Office Action for U.S. Appl. No. 10/434,636 (mailed Jun. 1, 2007).
Office Action for U.S. Appl. No. 10/235,238 (mailed Feb. 27, 2006).
Office Action for U.S. Appl. No. 10/235,238 (mailed Nov. 27, 2006).
Office Action for U.S. Appl. No. 10/435,406 (mailed Oct. 7, 2004).
Office Action for U.S. Appl. No. 10/435,406 (mailed Feb. 13, 2006).
Office Action for U.S. Appl. No. 10/435,406 (mailed Jun. 4, 2007).
Office Action for U.S. Appl. No. 10/434,607 (mailed Sep. 30, 2004).
Office Action for U.S. Appl. No. 10/434,607 (mailed Feb. 15, 2006).
Office Action for U.S. Appl. No. 10/434,607 (mailed Jun. 1, 2007).
Office Action for U.S. Appl. No. 10/305,747 (mailed Nov. 4, 2005).
Office Action for U.S. Appl. No. 10/305,747 (mailed May 23, 2006).
Office Action for U.S. Appl. No. 10/431,805 (mailed Sep. 30, 2004).
Office Action for U.S. Appl. No. 10/431,805 (mailed Dec. 20, 2005).
Office Action for U.S. Appl. No. 10/431,805 (mailed Jun. 1, 2007).
Office Action for U.S. Appl. No. 10/397,953 (mailed Sep. 30, 2004).
Office Action for U.S. Appl. No. 10/397,953 (mailed Feb. 15, 2006).
Office Action for U.S. Appl. No. 10/397,953 (mailed Nov. 2, 2007).
Office Action for U.S. Appl. No. 10/698,572 (mailed Jun. 15, 2007).
Office Action for U.S. Appl. No. 07/655,965 (mailed Feb. 24, 1992).
Office Action for U.S. Appl. No. 08/191,352 (mailed Sep. 2, 1994).
Office Action for U.S .Appl. No. 08/191,352 (mailed Apr. 4, 1995).
Office Action for U.S. Appl. No. 08/191,352 (mailed Dec. 22, 1995).
Office Action for U.S. Appl. No. 08/191,352 (mailed Sep. 9, 1996).
Office Action for U.S. Appl. No. 08/191,352 (mailed Apr. 30, 1997).
Office Action for U.S. Pat. No. 6,063,755 (mailed Sep. 9, 1996).
Office Action for U.S Pat. No. 6,063,755 (mailed Jun. 11, 1997).
Office Action for U.S. Pat. No. 6,063,755 (mailed Aug. 19, 1998).
Office Action for U.S. Pat. No. 6,063,755 (mailed May 24, 1999).
Office Action for U.S. Pat. No. 6,316,218 (mailed Jan. 22, 1999).
Office Action for U.S. Pat. No. 6,221,840 (mailed Apr. 2, 1997).
Office Action for U.S. Pat. No. 6,221,840 (mailed Jan. 6, 1998).
Office Action for U.S. Pat. No. 6,221,840 (mailed Apr. 2, 1999).
Office Action for U.S. PAt. No. 6,221,840 (mailed Dec. 27, 1999).
Office Action for U.S. Pat. No. 6,221,840 (mailed Jul. 10, 2000).
Office Action for U.S. Appl. No. 10/353,334 (mailed Feb. 8, 2007).
Office Action for U.S. Appl. No. 10/353,334 (mailed Oct. 22, 2007).
Office Action for U.S. Appl. No. 10/362,310 (mailed Feb. 12, 2007).
Office Action for U.S. Pat. No. 6,426,404 (mailed Jan. 20, 2000).
Office Action for U.S. Pat. No. 6,426,404 ( mailed Oct. 24, 2000).
Office Action for U.S. Pat. No. 6,426,404 (mailed Jul. 17, 2001).
Office Action for U.S. Pat. No. 6,525,018 (mailed Jul. 3, 2001).
Office Action for U.S. Pat. No. 6,525,018 (mailed Jun. 25, 2002).
Office Action for U.S. Appl. No. 10/313,642 (mailed Mar. 16, 2004).
Office Action for U.S. Appl. No. 10/313,642 (mailed Dec. 22, 2004).
Office Action for U.S. Appl. No. 10/313,642 (mailed Feb. 15, 2006).
Office Action for U.S. Appl. No. 10/313,642 (mailed Nov. 15, 2006).

Office Action for U.S. Appl. No. 10/449,456 (mailed Oct. 1, 2004).

Office Action for U.S. Appl. No. 10/449,456 (mailed Feb. 15, 2006).

Office Action for U.S. Appl. No. 10/449,456 (mailed Jun. 15, 2007).

Declaration under 37 C.F.R. §1.132 for U.S. Pat. Appl. No. 09/056,868 (executed Jun. 12, 1998).

Sequence alignment from European Pat. Appl. No. 97921148.9 (submitted to European Pat. Office on Aug. 7, 2006).

* cited by examiner

FIG. 1

```
gaagtttgcg tgctgcc                                                  17
atg gag acc aga gcc ttc tgg ata acc ctg ctg ctg gtc ctg gtt         62
gct ggg tcc tcc tgc aaa gcc cag gaa ttt gtt ggc cta tct cca        107
agc caa tgt atg gcg cca aca aat gtc agg gtg gac tgt aac tac        152
ccc act gtc aca tca gag cag tgt aac aac cgt ggt tgc tgt ttt        197
gac tcc agc atc cca aat gtg ccc tgg tgc ttc aaa cct ctg caa        242
gag aca gaa tgt aca ttt                                            260
tgaagctgtc caggctccag gaagggagct ccacaccctg gactcttgct             310
gatggtagtg gcccagggta acactcaccc ctgatctgct ccctcgcgcc             360
ggccaatata ggagctggga gtccagaaga ataaagacct tacagtcagc             410
acaaggctgt tctaattgcg g                                            431
```

FIG. 2

Met Glu Thr Arg Ala Phe Trp Ile Thr Leu Leu Leu Val Leu Val
5 10 15

Ala Gly Ser Ser Cys Lys Ala Gln Glu Phe Val Gly Leu Ser Pro
20 25 30

Ser Gln Cys Met Ala Pro Thr Asn Val Arg Val Asp Cys Asn Tyr
35 40 45

Pro Thr Val Thr Ser Glu Gln Cys Asn Asn Arg Gly Cys Cys Phe
50 55 60

Asp Ser Ser Ile Pro Asn Val Pro Trp Cys Phe Lys Pro Leu Gln
65 70 75

Glu Thr Glu Cys Thr Phe
80

FIG. 3

```
rITF   METRAFWITLLLVLVAGSSCKAQEFVGLSPSQCMAPTNVRVDCNYPTVTSEQCNNRGCC
       ---------------------------------------------------------
pS2    ----------------EAQ------TETCTVAPRERQNCGFPGVTPSQCANKGCC
PSP    ----------------------EKPAACRCSRQDPKN-RVNCGFPGITSDQCFTSGCC

rITF   FDSSIPNVPWCFK-----PLQ-----ETECT-----F
       ---------------------------------------
pS2    FDDTVRGVPWCFY-----PNTIDVPPEEECE-----F
       ---------------------------------------
PSP    FDSQVPGVPWCFK-----PLP-----AQESEECVMEV
```

FIG. 6

```
g atg ctg ggg ctg gtc ctg gcc ttg ctg tcc tcc agc tct gct gag gag      49
  Met Leu Gly Leu Val Leu Ala Leu Leu Ser Ser Ser Ser Ala Glu Glu
    1               5                   10                  15

tac gtg ggc ctg tct gca aac cag tgt gcc gtg ccg gcc aag gac agg        97
Tyr Val Gly Leu Ser Ala Asn Gln Cys Ala Val Pro Ala Lys Asp Arg
            20                  25                  30
gtg gac tgc ggc tac ccc cat gtc acc ccc aag gag tgc aac aac cgg       145
Val Asp Cys Gly Tyr Pro His Val Thr Pro Lys Glu Cys Asn Asn Arg
        35                  40                  45
ggc tgc tgc ttt gac tcc agg atc cct gga gtg cct tgg tgt ttc aag       193
Gly Cys Cys Phe Asp Ser Arg Ile Pro Gly Val Pro Trp C   P   K
    50                  55                  60

ccc ctg cag gaa gca gaa tgc acc ttc tgaggcacct ccagctgccc             243
P   L   Q   E   A   E   C   T   F
65                  70

ctgggatgca ggctgagcac ccttgcccgg ctgtgattgc tgccaggcac tgttcatctc     303
agtttttctg tccctttgct cccggcaagc tttctgctga aagttcatat ctggagcctg     363
atgtcttaac gaataaaggt cccatgctcc acccgaaaaa                           403
```

FIG. 9

```
                gag aaa ccc tcc ccc tgc cag tgc tcc agg ctg agc
                Glu Lys Pro Ser Pro Cys Gln Cys Ser Arg Leu Ser
                  1               5                   10

ccc cat aac agg acg aac tgc ggc ttc cct gga atc acc agt gac cag
Pro His Asn Arg Thr Asn Cys Gly Phe Pro Gly Ile Thr Ser Asp Gln
         15                  20                  25

tgt ttt gac aat gga tgc tgt ttc gac tcc agt gtc act ggg gtc ccc
Cys Phe Asp Asn Gly Cys Cys Phe Asp Ser Ser Val Thr Gly Val Pro
     30              35                      40

tgg tgt ttc cac ccc ctc cca aag caa gag tcg gat cag tgc gtc atg
Trp Cys Phe His Pro Leu Pro Lys Gln Glu Ser Asp Gln Cys Val Met
 45                  50                  55                  60

gag gtc tca gac aga aga aac tgt ggc tac ccg ggc atc agc ccc gag
Glu Val Ser Asp Arg Arg Asn Cys Gly Tyr Pro Gly Ile Ser Pro Glu
                 65                  70                  75

gaa tgc gcc tct cgg aag tgc tgc ttc tcc aac ttc atc ttt gaa gtg
Glu Cys Ala Ser Arg Lys Cys Cys Phe Ser Asn Phe Ile Phe Glu Val
             80                  85                  90

ccc tgg tgc ttc ttc ccg aac tct gtg gaa gac tgc cat tac
Pro Trp Cys Phe Phe Pro Asn Ser Val Glu Asp Cys His Tyr
         95                  100                 105
```

FIG. 10

```
atccctgact cggggtcgcc tttggagcag agaggaggca atg gcc acc atg gag      55
                                            Met Ala Thr Met Glu
                                             1               5

aac aag gtg atc tgc gcc ctg gtc ctg gtg tcc atg ctg gcc ctc ggc     103
Asn Lys Val Ile Cys Ala Leu Val Leu Val Ser Met Leu Ala Leu Gly
                10                  15                  20

acc ctg gcc gag gcc cag aca gag acg tgt aca gtg gcc ccc cgt gaa     151
Thr Leu Ala Glu Ala Gln Thr Glu Thr Cys Thr Val Ala Pro Arg Glu
            25                  30                  35

aga cag aat tgt ggt ttt cct ggt gtc acg ccc tcc cag tgt gca aat     199
Arg Gln Asn Cys Gly Phe Pro Gly Val Thr Pro Ser Gln Cys Ala Asn
        40                  45                  50

aag ggc tgc tgt ttc gac gac acc gtt cgt ggg gtc ccc tgg tgc ttc     247
Lys Gly Cys Cys Phe Asp Asp Thr Val Arg Gly Val Pro Trp Cys Phe
    55                  60                  65

tat cct aat acc atc gac gtc cct cca gaa gag gag tgt gaa ttt         292
Tyr Pro Asn Thr Ile Asp Val Pro Pro Glu Glu Glu Cys Glu Phe
70                  75                  80

tagacacttc tgcagggatc tgcctgcatc ctgacggggt gccgtcccca gcacggtgat   352
tagtcccaga gctcggctgc cacctccacc ggacacctca gacacgcttc tgcagctgtg   412
cctcggctca caacacagat tgactgctct gactttgact actcaaaatt ggcctaaaaa   472
ttaaaagaga tcgatattaa aaaaaaaaaa aaaaaaaaaa aaaaaaaaaa aaaaaaaaaa   532
aaaaaaaa                                                            540
```

TREATING EYE DISORDERS INTESTINAL TREFOIL PROTEINS

Matter enclosed in heavy brackets [ ] appears in the original patent but forms no part of this reissue specification; matter printed in italics indicates the additions made by reissue.

*CROSS-REFERENCE TO RELATED APPLICATIONS*

*This application is a reissue of U.S. application Ser. No. 09/313,434, filed May 17, 1999, issued as U.S. Pat. No. 6,525,018, which is a continuation-in-part of U.S. application Ser. No. 10/362,310, filed Feb. 19, 2003, which is the National Stage of International Application No. PCT/US97/06004, filed Apr. 11, 1997, which was published in English under PCT Article 21(2), and which is a continuation-in-part of U.S. application Ser. No. 08/631,469, filed Apr. 12, 1996, issued as U.S. Pat. No. 6,221,840, each of which is hereby incorporated by reference.*

FIELD OF THE INVENTION

The field of the invention is peptides useful for treatment of disorders of the digestive system, disorders of the eye and disorders associated with unwanted apoptosis.

BACKGROUND

Jørgensen et al. (1982, Regulatory Peptides 3:231) describe a porcine pancreatic peptide, pancreatic spasmolytic peptide (PSP). PSP was found to inhibit "gastrointestinal motility and gastric acid secretion in laboratory animal after parenteral as well as oral administration." It was suggested that "if the results in animal experiments can be confirmed in man, PSP may possess a potential utility in treatment of gastroduodenal ulcer diseases."

pS2 is a small cysteine-rich protein which is expressed and secreted from human breast tumours. In addition, pS2 protein is expressed in normal stomach mucosa and in regenerative tissues in ulcerative diseases of the gastrointestinal tract (Rio et al., Cancer Cells, 1990, 2:269–74).

SUMMARY OF THE INVENTION

In a first aspect, the invention features a purified nucleic acid encoding an intestinal trefoil factor (ITF).

In preferred embodiments, the ITF is a mammalian ITF, preferably human, rat, bovine, mouse, monkey or porcine ITF. In another preferred embodiment, the purified nucleic acid encoding an ITF is present within a vector. In one embodiment, the ITF is in a monomer form. In another embodiment, two monomer ITF can be linked by a disulfide bond to form a dimer.

In a related aspect, the invention features a cell that includes a vector encoding an ITF.

In another related aspect, the invention features a substantially pure ITF. In a preferred embodiment, the polypeptide is detectably labelled. In a related aspect, the invention features a therapeutic composition that includes an ITF and a pharmacologically acceptable carrier.

In another aspect the invention features ITF variants.

In another aspect, the invention features a monoclonal antibody which preferentially binds (i.e., forms an immune complex with) an ITF. In a preferred embodiment, the monoclonal antibody is detectably labelled.

In a related aspect, the invention features a method for detecting human ITF in a human patient. The method includes the steps of contacting a biological sample obtained from the patient with a monoclonal antibody which preferentially binds ITF, and detecting immune complexes formed with the monoclonal antibody. In preferred embodiments the biological sample is an intestinal mucosal scraping, or serum.

In a related aspect, the invention features a method for treating digestive disorders in a human patient, which method involves administering to the patient a therapeutic composition that includes an ITF and a pharmacologically acceptable carrier. In one embodiment, a wild-type ITF protein, e.g., a human ITF protein (FIG. 6, SEQ ID NO:4), is used to treat a digestive disorder. A wild-type ITF protein is resistant to destruction in the digestive tract, and can be used for treatment of a digestive disorder such as a peptic ulcer diseaase, an inflammatory bowel disease, and can be used to protect the intestinal tract from injury caused by insults such as radiation injury or bacterial infection.

In another related aspect, the invention features a method for treating an eye disorder in a human patient, which method involves administering to the patient a therapeutic composition that includes an ITF protein and a pharmacologically acceptable carrier. An ITF protein and biologically active fragments or variants thereof can be used for the treatment of eye disorders such as a corneal ulcer, or an ocular inflammatory disease. An ITF and biologically active fragments or variants thereof can be used to treat corneal injury or lesion associated with corneal transplantation, lens implantation and other types of eye surgery. ITF can also be used to treat traumatic physical injury to the eye. The methods of the invention also include treating eye disorders with SP or pS2 protein, e.g., a human Sp or pS2 protein (FIG. 9, SEQ ID NO:14 and FIG. 10, SEQ ID NO:16), respectively. In addition, biologically active fragments or variants of SP or pS2 can be used to treat eye disorders. Any or all of the trefoil proteins can be administered to treat an eye disorder (see Sands, Annual Rev. Physiol 58:253–73). ITF or pS2 can be administered in monomer form or can be administered in a dimer form.

In yet another related aspect, the invention features a method for modulating apoptosis in a human patient, which method involves administering to the patient a therapeutic composition that modulates expression or activity of ITF and a pharmacologically acceptable carrier. The methods of the invention also include a method of modulating apoptosis by administering a therapeutic composition that modulates expression or activity of SP or pS2. In addition, biologically active fragments or variants of SP or pS2 can be used to modulate apoptotic disorders. Any or all of the trefoil proteins can be administered. ITF or pS2 can be administered in monomer form or can be administered in a dimer form.

In another aspect, the invention features a method for detecting binding sites for ITF in a patient. The method involves contacting a biological sample obtained from the patient with the factor, and detecting the factor bound to the biological sample as an indication of the presence of the binding sites in the sample. By "binding sites," as used herein, is meant any antibody or receptor that binds to an ITF protein, factor, or analog. The detection or quantitation of binding sites may be a useful reflection of abnormalities of the digestive tract.

In another aspect, the invention features substantially pure ITF. In preferred embodiments, the ITF is human, porcine, mouse, rat, guinea pig, monkey, or bovine trefoil factor.

By "intestinal trefoil factor" ("ITF") is meant any protein that is substantially homologous to rat ITF (FIG. 2, SEQ ID NO.:2) or human ITF (FIG. 6, SEQ ID NO:4) and which is expressed in the large intestine, small intestine, or colon to a greater extent than it is expressed in tissues other than the small intestine, large intestine, or colon. Also included are: allelic variations; natural mutants; induced mutants; proteins encoded by DNA that hybridizes under high or low stringency conditions to ITF encoding nucleic acids retrieved from naturally occurring material; and polypeptides or proteins retrieved by antisera to ITF, especially by antisera to the active site or binding domain of ITF. The term also includes other chimeric polypeptides that include an ITF.

The term ITF also includes analogs of naturally occurring ITF polypeptides. Analogs can differ from the naturally occurring ITF by amino acid sequence differences or by modifications that do not affect sequence, or by both. Analogs of the invention will generally exhibit at least 70%, more preferably 80%, more preferably 90%, and most preferably 95% or even 99%, homology with all or part of a naturally occurring ITF sequence. The length of comparison sequences will generally be at least 8 amino acid residues, usually at least 20 amino acid residues, more usually at least 24 amino acid residues, typically at least 28 amino acid residues, and preferably more than 35 amino acid residues. Modifications include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps, e.g., by exposing the polypeptide to enzymes that affect glycosylation derived from cells that normally provide such processing, e.g., mammalian glycosylation enzymes. Also embraced are versions of the same primary amino acid sequence that have phosphorylated amino acid residues, e.g., phosphotyrosine, phosphoserine, or phosphothreonine. Analogs can differ from naturally occurring ITF by alterations of their primary sequence. These include genetic variants, both natural and induced. Induced mutants may be derived by various techniques, including random mutagenesis of the encoding nucleic acids using irradiation or exposure to ethanemethylsulfate (EMS), or may incorporate changes produced by site-specific mutagenesis or other techniques of molecular biology. See, Sambrook, Fritsch and Maniatis (1989), Molecular Cloning: A Laboratory Manual (2d ed.), CSH Press, hereby incorporated by reference. Also included are analogs that include residues other than naturally occurring L-amino acids, e.g., D-amino acids or non-naturally occurring or synthetic amino acids, e.g., β or γ amino acids.

In addition to substantially full-length polypeptides, the term ITF, as used herein, includes A biologically active fragments of the polypeptides. As used herein, the term "fragment," as applied to a polypeptide, will ordinarily be at least 10 contiguous amino acids, typically at least 20 contiguous amino acids, more typically at least 30 contiguous amino acids, usually at least 40 contiguous amino acids, preferably at least 50 contiguous amino acids, and most preferably at least 60 to 80 or more contiguous amino acids in length. Fragments of ITF can be generated by methods known to those skilled in the art and described herein. The ability of a candidate fragment to exhibit a biological activity of ITF can be assessed by methods known to those skilled in the art and are described herein. Also included in the term "fragment" are biologically active ITF polypeptides containing amino acids that are normally removed during protein processing, including additional amino acids that are not required for the biological activity of the polypeptide, or including additional amino acids that result from alternative mRNA splicing or alternative protein processing events.

An ITF polypeptide, fragment, or analog is biologically active if it exhibits a biological activity of a naturally occurring ITF, e.g., the ability to alter gastrointestinal motility in a mammal or the ability to enhance corneal epithelial wound healing.

The invention also includes nucleic acid sequences, and purified preparations thereof, that encode the ITF polypeptides described herein. The invention also includes antibodies, preferably monoclonal antibodies, that bind specifically to ITF polypeptides.

ITF, SP and pS2 are referred to as trefoil proteins and are members of the trefoil family. These proteins are designated trefoil proteins because they have a trefoil shaped secondary structure which is stabilized by intrachain disulfide bonds. Members of the trefoil family typically will have at least one of the following properties in common: (i) a common structural domain, e.g., the trefoil shaped secondary structure, (ii) a degree of amino acid or nucleotide sequence homology, or (iii) a common functional characteristic.

Members of the trefoil family, e.g., ITF, are used in the treatments discussed above. Skilled artisans may review these proteins in Sands et al. (1996, Ann. Rev. Physiol. 58:253–273). As stated above, the invention encompasses biologically active fragments of the trefoil proteins. Fragments that retain the trefoil structure (i.e., the three loop structure) or that lie within regions of the protein that are highly conserved may prove particularly useful. Thus, portions of ITF, pS2, or SP from about the first cystine involved in a disulfide bond of the three loop structure to about the last cysteine involved in a disulfide bond of the three loop structure are useful. Biologically active fragments of ITF, pS2, SP can include 5, 10, 20, 30, 40, 50, 60, 70, 80, 90, 100, 110, 120, or 129 amino acids.

Variants of a selected trefoil protein are least 60%, preferably at least 75%, more preferably at least 90%, and most preferably at least 95% identical to the selected trefoil protein, preferably a human trefoil protein, more preferably human ITF.

The term "identical," as used herein in reference to polypeptide or DNA sequences, refers to the subunit sequence identity between two molecules. To determine the percent sequence identity of two amino acid sequences or of two nucleic acids, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In one embodiment the two sequences are the same length.

The determination of percent identity between two sequences can be accomplished using a mathematical algorithm. A preferred, non-limiting example of a mathematical algorithm utilized for the comparison of two sequences is the algorithm of Karlin and Altschul (1990) Proc. Natl. Acad. Sci. USA 87:2264–2268, modified as in Karlin and Altschul (1993) Proc. Natl. Acad. Sci. USA 90:5873–5877. Such an algorithm is incorporated into the NBLAST and XBLAST programs of Altschul, et al. (1990) J. Mol. Biol.

215:403–410. BLAST nucleotide searches can be performed with the NBLAST program, score=100, wordlength=12 to obtain nucleotide sequences homologous to a nucleic acid molecules of the invention. BLAST protein searches can be performed with the XBLAST program, score=50, wordlength=3 to obtain amino acid sequences homologous to a protein molecules of the invention. To obtain gapped alignments for comparison purposes, Gapped BLAST can be utilized as described in Altschul et al. (1997) Nucleic Acids Res. 25:3389–3402. Alternatively, PSI-Blast can be used to perform an iterated search which detects distant relationships between molecules (Id.). When utilizing BLAST, Gapped BLAST, and PSI-Blast programs, the default parameters of the respective programs (e.g., XBLAST and NBLAST) can be used. See http://www.ncbi.nlm.nih.gov. Another preferred, non-limiting example of a mathematical algorithm utilized for the comparison of sequences is the algorithm of Myers and Miller, (1988), CABIOS 4:11–17. Such an algorithm is incorporated into the ALIGN program (version 2.0) which is part of the GCC sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, only exact matches are counted.

An isolated nucleic acid molecule encoding a "variant protein" can be created by introducing one or more nucleotide substitutions, additions or deletions into the nucleotide sequence of ITF, pS2 or SP such that one or more amino acid substitutions, additions or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed recombinantly and the activity of the protein can be determined.

In the case of amino acid sequences that are less than 100% identical to a reference sequence, the non-identical positions are preferably, but not necessarily, conservative substitutions for the reference sequence. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine. Sequence identity is typically measured using sequence analysis software such as the Sequence Analysis Software Package of the Genetics Computer Group at the University of Wisconsin (Biotechnology Center, 1710 University Avenue, Madison, Wis. 53705), and the default parameters specified therein.

A variant of a selected trefoil protein preferably has the amino acids present in the naturally-occurring form of the selected trefoil protein at the more highly conserved amino acid positions of the protein. Thus, a variant of human ITF preferably is identical to naturally-occurring human ITF at all or nearly all of the more highly conserved positions. Sequence conservation among trefoil proteins is evident in Table 1 of Sands et al. (supra) which can be used by those skilled in the art to identify more conserved residues. In one embodiment, a human SP variant polypeptide is identical to wild-type SP polypeptide at 129 (127, 125, 123, 121, 119, 117, or 115) of the 130 amino acid residues of the wild-type SP. Preferably the cysteine residues and the trefoil structure is preserved. The remaining amino acids can be replaced by conservative substitutions. In another embodiment, a human pS2 variant polypeptide is identical to wild type pS2 at 83 (81, 79, 77, 75, 73, 72, or 71) of the 84 amino acid residues of the wild-type pS2. Preferably the cysteine residues and the trefoil structure is preserved. The remaining pS2 amino acid residues can be replaced by conservative substitutions. In yet another embodiment, a human ITF variant polypeptide is identical to wild-type human ITF at 72 (71, 69, 67, 65, 63, 61 or 59) of the 73 amino acid residues of the wild-type human ITF. Preferably the cysteine residues and the trefoil structure is preserved. The remaining amino acids can be replaced by conservative substitutions.

As used herein, the term "substantially pure" describes a compound, e.g., a nucleic acid, a protein, or a polypeptide, e.g., an ITF protein or polypeptide, that is substantially free from the components that naturally accompany it. Typically, a compound is substantially pure when at least 60%, more preferably at least 75%, more preferably at least 90%, and most preferably at least 99%, of the total material (by volume, by wet or dry weight, or by mole per cent or mole fraction) in a sample is the compound of interest. Purity can be measured by any appropriate method, e.g., in the case of polypeptides, by column chromatography, polyacrylamide gel electrophoresis, or HPLC analysis.

By "isolated DNA" is meant DNA that is free of the genes which, in the naturally-occurring genome of the organism from which the given DNA of the invention is derived, flank the DNA. The term "isolated DNA" thus encompasses, for example, cDNA, cloned genomic DNA, and synthetic DNA. A "purified nucleic acid", as used herein, refers to a nucleic acid sequence that is substantially free of other macromolecule (e.g., other nucleic acids and proteins) with which it naturally occurs within a cell. In preferred embodiments, less than 40% (and more preferably less than 25%) of the purified nucleic acid preparation consists of such other macromolecule.

"Homologous", as used herein, refers to the subunit sequence similarity between two polymeric molecules, e.g., between two nucleic acid molecules, e.g., two DNA molecules, or two polypeptide molecules. When a subunit position in both of the molecules is occupied by the same monomeric subunit, e.g., if a position in each of two DNA molecules is occupied by adenine, then they are homologous at that position. The homology between two sequences is a direct function of the number of matching or homologous positions, e.g., if half, e.g., 5 of 10, of the positions in two compound sequences are homologous then the two sequences are 50% homologous; if 90% of the positions, e.g., 9 of 10, are matched or homologous the two sequences share 90% homology. By way of example, the DNA sequences 3'ATTGCC'5 and 3'TATGGC'5 share 50% homology. By "substantially homologous" is meant largely but not wholly homologous.

"Treatment of lesions" encompasses both the inhibition of the formation of lesion and the healing of lesions already formed. Biologically active fragments and variants of a trefoil protein, particularly ITF, which promote healing of lesions, e.g., eye lesion, intestinal lesion, or inhibit the formation of lesions,e.g., eye lesions or intestinal lesions, are useful in the treatments of the invention.

"Disorders of the eye" refers to any disturbance, defect, or abnormality in eye function or structure (e.g., the eye disorder is a disorder resulting from a disruption of the corneal epithelium). An eye disorder can be congenital, hereditary, or can be the result of a trauma such as a physical injury, an illness, inflammation, an autoimmune disease, a virus (e.g., adenoviruses, herpes simplex virus), a blepharitis, a keratitis sicca, a trachoma, a corneal foreign body, ultraviolet light exposure (e.g., welding arcs, sunlamps), contact lens overwear, a systemic drug (e.g., adenine arabinoside), a tropical drug, or invasion by a microbe.

Other features and advantages of the invention will be apparent from the following description of the preferred embodiments thereof, and from the claims.

BRIEF DESCRIPTION OF THE DRAWINGS

FIG. 1 is a depiction of the nucleotide sequence of rat trefoil factor (SEQ ID NO.:1).

FIG. 2 is a depiction of the deduced amino acid sequence of rat trefoil factor (SEQ ID NO.:2).

FIG. 3 is a depiction of the amino acid sequences of rat trefoil factor (SEQ ID NO:2), pS2 protein (SEQ ID NO:11), and pancreatic spasmolytic polypeptide (SP) (SEQ ID NO:12). The sequences are aligned to illustrate the amino acid sequence homology between the proteins. Dashes (–) indicate the insertion of spaces which optimize alignment. Bars indicate sequence identity.

FIG. 6 is a depiction of the nucleotide sequence of the human ITF cDNA (SEQ ID NO:3) and the corresponding deduced amino acid sequence (SEQ ID NO:4).

FIG. 9 is a depiction of the nucleotide sequence of the mature human spasmolytic cDNA and the corresponding deduced amino acid sequence (SEQ ID NO:13 and 14, respectively).

FIG. 10 is a depiction of the nucleotide sequence of the human pS2 cDNA and the corresponding deduced amino acid sequence (SEQ ID NO:15 and 16, respectively).

DETAILED DESCRIPTION

Treatment of Digestive Tract Disorders

Figure 4A:
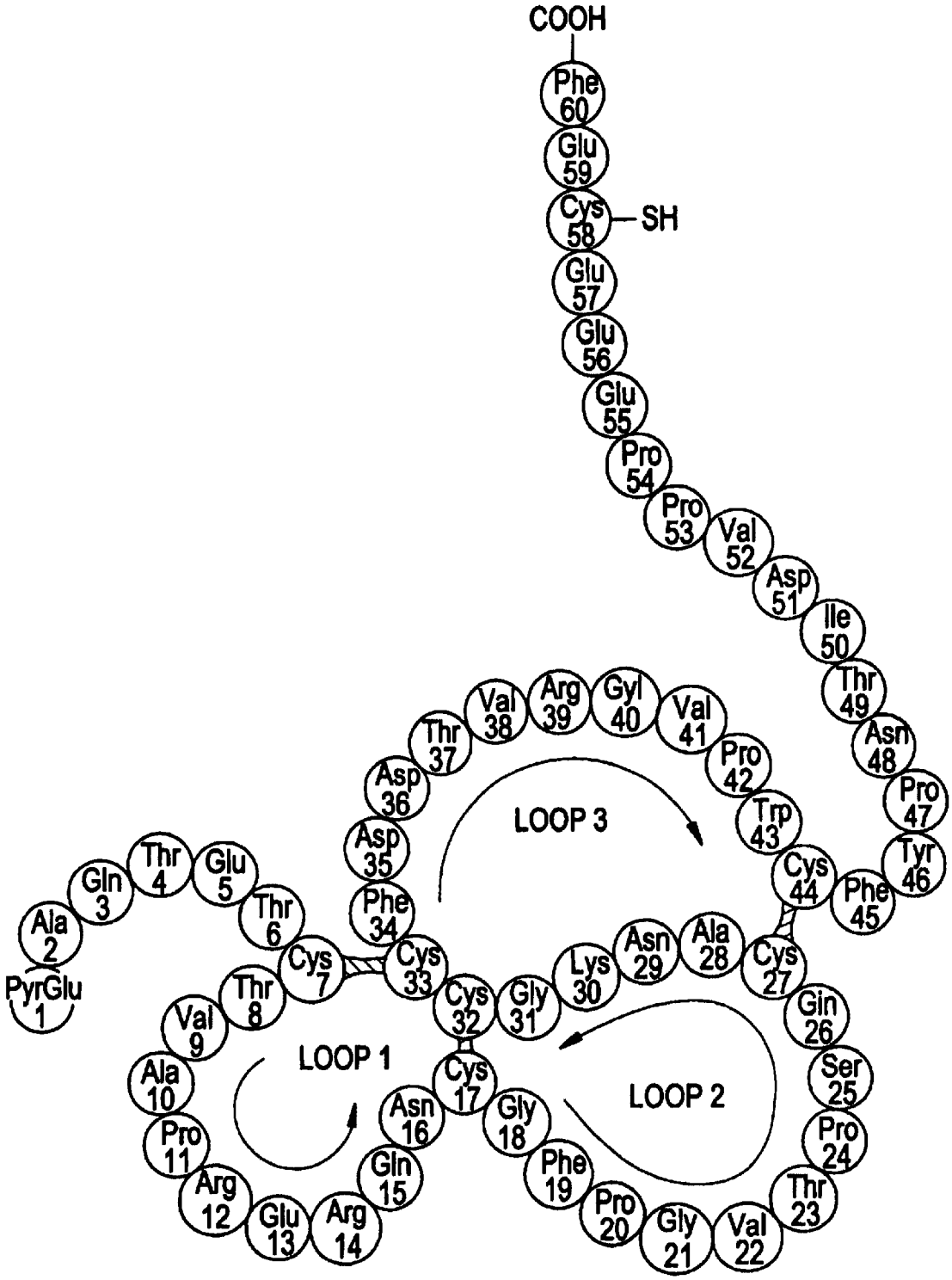
FIG. 4 depicts the disulfide bond structure proposed for pS2 (panel A) and PSP (panel B).

Trefoil proteins, and in particular ITF, can be used to treat a number of different conditions. ITF is useful for treatment of disorders associated with digestive tract because of its generally protective effect on the digestive tract. ITF promotes the maintenance of mucosal integrity. ITF can also be used to inhibit adhesion to or colonization of the mucosa by Helicobacter pylori (H. pylori). H. pylori is one of the most common bacterial infections leading to active, chronic gastritis and is frequently associated with syndromes such as duodenal ulcer, gastric ulcer, gastric cancer, MALT lymphoma, or Menetrier's syndrome. Eradication of H. plyori has been shown to reduce the recurrence of duodenal and gastric ulcers. Furthermore, it has been postulated that widespread treatment of H. plyori will reduce the incidence of gastric carcinoma, which is the second leading cause of cancer related death world-wide.

Long-standing gastritis associated with H. plyori infection is often associated with the expression of intestinal-like features in the gastric mucosa. This condition, referred to as intestinal metaplasia (IM), may signal an increased risk of gastric cancer. The etiology of IM is unclear, it could represent a mutation adaptation or defense against H. plyori infection. For example, the metaplastic mucosa may produce mucus or other substances that create an environment that is hostile to H. plyori. ITF can be used in the treatment of H. plyori infection and conditions associated with H. plyori infection (e.g., ulcers, gastric carcinoma, non-ulcer dyspepsia, gastritis, and esophageal lesions associated with gastro-esophageal reflux disease). In this application ITF or fragments or variants thereof which inhibit adhesion or colonization of the mucosa by H. plyori are useful. Such molecules can be identified using assays known to those skilled in the art, including the H. plyori binding assay described below.

ITF may also be used to promote healing of tissues damaged by conditions associated with H. plyori infection. In this regard, it is important that addition of trefoil proteins to wounded monolayers of confluent intestinal epithelial cells increases the rate of epithelial cell migration into the wound. This effect is enhanced by concomitant addition of mucin glycoproteins, the other dominant product of goblet cells.

Just as ITF can be used to protect other parts of the digestive tract, it can be used to protect the mouth and esophagus from damage caused by radiation therapy or chemotherapy. ITF can also be used to protect against and/or to treat damage caused by alcohols or drugs generally.

The invention features a method for the treatment of lesions in the alimentary canal of a patient by administering to the patient a trefoil peptide, or a biologically active fragment thereof. The lesions typically occur in the mucosa of the alimentary canal, and may be present in the mouth, esophagus, stomach, or intestine of the patient. The lesions can be caused in several ways. For example, the patient may be receiving radiation therapy or chemotherapy for the treatment of cancer. These treatments typically cause lesions in the mouth and esophagus of the patient. Skilled artisans will recognize that it may be useful to administer the proteins of the invention to the patient before such treatment is begun. Alternatively, the lesions can be caused by: (1) any other drug, including alcohol, that damages the alimentary canal, (2) accidental exposure to radiation or to a caustic substance, (3) an infection, or (4) a digestive disorder including but not limited to non-ulcer dyspepsia, gastritis, peptic or duodenal ulcer, gastric cancer, MALT lymphoma, Menetrier's syndrome, gastro-esophageal reflux disease, and Crohn's disease. For the treatment of human patients it is expected that the peptide will be expressed by a human gene. However, eukaryotic ITF proteins, such as those cloned from the rat and mouse genomes may also prove effective. These peptides may be isolated from a naturally occurring source or synthesized by recombinant techniques. It is expected that the typical route of administration will be oral. Determining other routes of administration, and the effective dosage are well within the skills of ordinary artisans and will depend on many factors known to these artisans.

Treatment of Eye Disorders

Injury to the corneal epithelium results in the rapid formation of a layer of cells that covers the denuded corneal surface, preventing infection and loss of vision. After wounding, resealing of the surface epithelium occurs over a period of several hours, resulting in the formation of a migratory leading edge. Proliferation through mitotic burst is observed in cells surrounding the original wound margin after 36 hours.

The invention features a method for treating an eye disorder (trauma or lesion) in a patient. The method involves administering to the patient a trefoil peptide, or a biologically active fragment thereof. In one embodiment, trefoil can be administered to a patient having a corneal transplant. A trefoil protein (e.g., ITF, pS2, SP and biologically active fragments or variants thereof) can be used to treat an eye condition. A trefoil protein, and biologically active fragments or a variants thereof can also be used to maintain eye structural integrity and protect the eye. Biologically active fragments or variants of a trefoil protein can be identified using assays known to those skilled in the art, including the in vitro or in vivo eye assay's described below. ITF or pS2 can be administered as a monomer or as a dimer.

An eye disorder may affect any part of the eye, e.g., the cornea, the sclera, the retina, the conjunctiva, the ciliary body, the posterior chamber, or the anterior chamber. In a preferred embodiment the eye disorder affects the cornea, e.g., the corneal epithelium, or the conjunctiva. Eye disorders include but are not limited to superficial puntate keratitis, corneal ulcer, herpes simplex keratoconjunctivitis, ophthalmic herpes zoster, phlyctenular keratoconjunctivitis, keratoconus, conjunctiva, keratoconjunctivitis sicca (dry eyes), ocular inflammation, corneal ulcers and cicatricial penhigoid. Eye disorders can be caused by viruses (e.g., adenoviruses, herpes simplex virus), blepharitis, keratitis sicca, trachoma, corneal foreign bodies, ultraviolet light exposure (e.g., welding arcs, sunlamps), contact lens overwear, systemic drugs (e.g., adenine arabinoside), tropical drugs, bacteria, fungi, or by a hypersensensitive reaction to an unknown antigen. Physical eye trauma can also result in an eye disorder. Physical trauma to the eye includes an abrasion to the cornea (e.g., caused by a foreign body), perforation of the cornea (e.g., caused by a blunt injury that disrupts the continuity of the cornea), or chemical burns to the cornea (e.g., exposure to NaOH). The eye disorder generally results in damage and disruption of eye function or structure. For example, the disorder may cause the corneal epithelium to tear, cause necrosis of the cornea, cause corneal ulcers or damage the conjunctiva. Any of the eye disorders listed above can be treated by administering trefoil. For the treatment of human patients with eye disorders it is expected that the trefoil protein will be expressed by a human gene. However, eukaryotic trefoil proteins, such as those cloned from the rat and mouse genomes may also prove effective. These proteins may be isolated from a naturally occurring source or synthesized by recombinant techniques. It is expected that the typical route of administration will be topical. Determining other routes of administration, and the effective dosage are well within the skill of an ordinary artisan and will depend on many factors known to the artisan and can be determined based on studies in animal models and humans. The trefoil proteins may be administered singly, or in combination with another protein/preparation.

Modulating Apoptosis

In another related aspect, the invention features a method for modulating apoptosis (e.g., the method includes inhibiting unwanted apoptosis) in a patient, which method involves administering to the patient a therapeutic composition that modulates expression or activity of a trefoil protein. The method also includes administering a trefoil or a biologically active fragment thereof in order to inhibit aberrant apoptosis, activate apoptosis or enhance apoptosis in a patient. Unwanted apoptosis includes any condition where a patient has abnormal apoptosis. These conditions include but are not limited to the following: retinitis pigmentosa, Alzheimer's disease, Parkinson's disease, amyotrophic lateral sclerosis (ALS), spinal muscular atrophy, various forms of cerebellar degeneration, decreased production of blood cells, chronic neutrophenia, myelodysplastic syndromes, myocardial infarctions and stroke.

EXAMPLE 1

Purification and Cloning of rITf

This example details how rat ITF was cloned. An inhibitor of soft agar colony formation by human breast carcinoma-derived BT-20 cells (ATTC HTB79) was isolated from cytology-positive human malignant effusions (Podolsky et al., 1988, Cancer Res. 48:418; hereby incorporated by reference). The factor also inhibited soft agar colony formation by human colon carcinoma-derived HCT15 cells (ATTC-CCL225). Inhibition was not observed for polyoma and murine sarcoma virus transformed rodent fibroblast lines. The isolated factor (transformed cell-growth inhibiting factor or TGIF) had an apparent molecular weight of 110,000 kD and appeared to consist of two 55,000 kD subunits linked by sulfhydryl bonds.

The purified protein was partially sequenced. The sequence form the amino terminal 14 amino acids was used to produce a set of degenerate oligonucleotide probes for screening of a rat intestinal epithelial cell cDNA library.

A rat intestinal cDNA library (Lambda ZAP° II, Stratagene, La Jolla, Calif.) was produced by standard techniques (Ausubel et al., Eds., Current Protocols in Molecular Biology, John Wiley & Sons, New York, 1989) using cells purified by the method of Weisner (1973, J. Biol Chem. 248:2536). Screening of the cDNA library with the fully degenerate oligonucleotide probe described above resulted in the selection of 21 clones. One of the clones (T3411) included a core sequence which encoded a single open reading frame. The nucleotide sequence of the open reading frame and flanking DNA is presented in FIG. 1 (SEQ ID NO.:1). The insert present in T3411 was nick translated (Ausubel et al., supra) to produce a radioactively labelled probe for Northern blot analysis of rat poly(A)$^+$ RNA. Northern analysis demonstrated that RNA corresponding to the cloned cDNA fragment was expressed in small intestine, large intestine, and kidney; no expression was detected in the lung, spleen, heart, testes, muscle, stomach, pancreas, or liver. In the tissues in which the RNA was expressed, the level was comparable to that of actin.

Figure 4B:
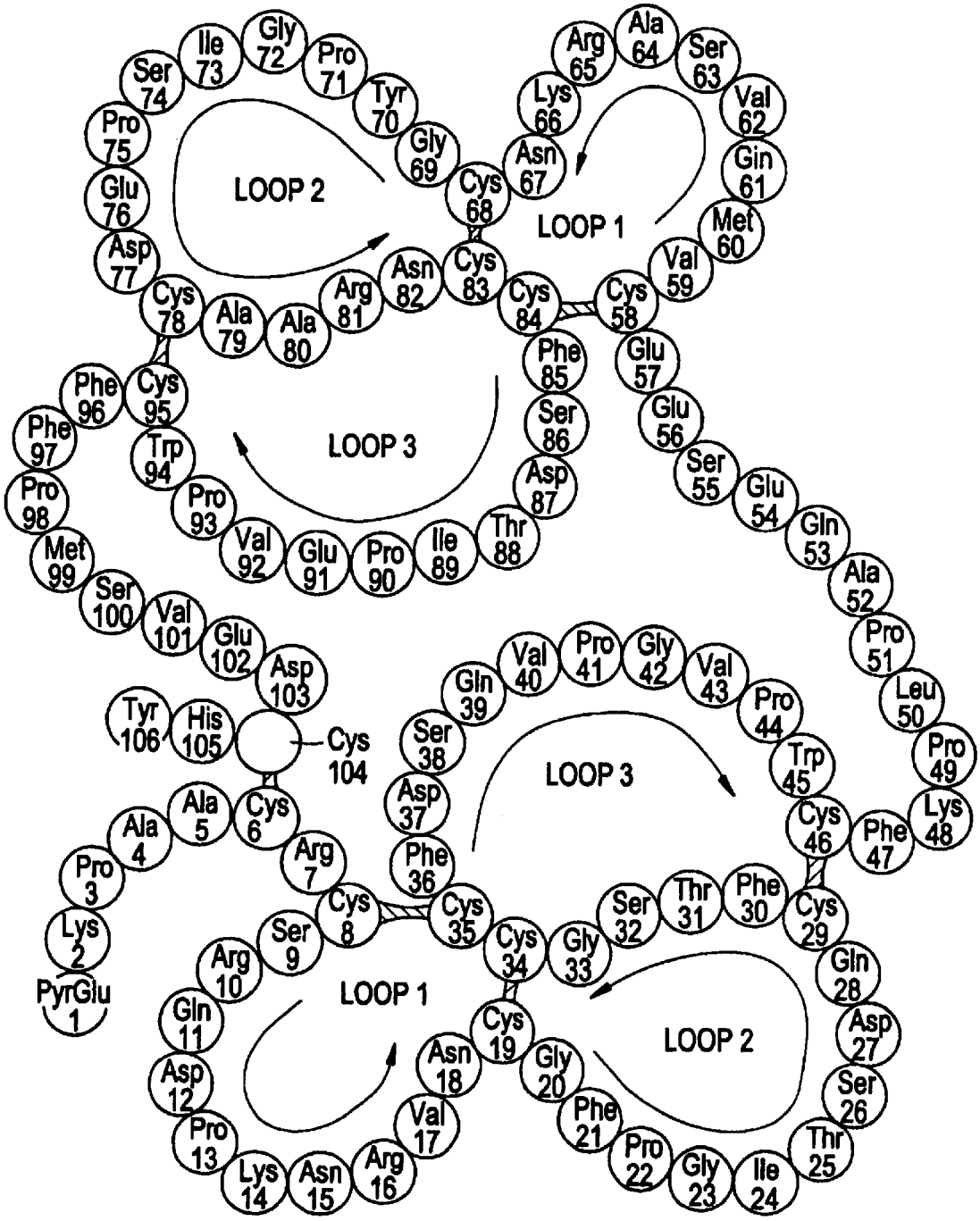
Figure 5:
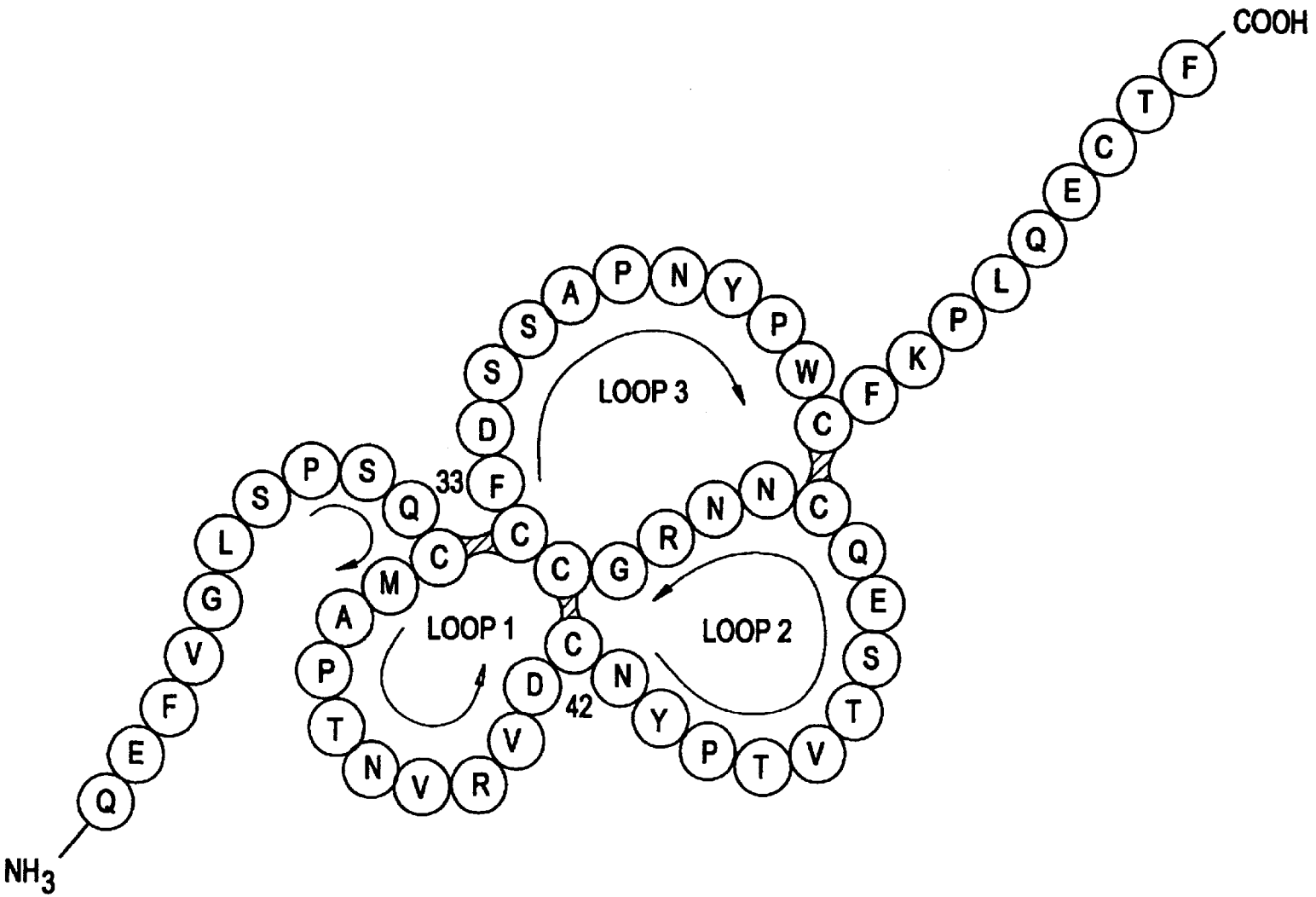
FIG. 5 is a depiction of the proposed disulfide bond structure of rat ITF (residues 23–81 of SEQ ID NO:2).

The open reading frame of clone T3411 encoded an 81 amino acid peptide (FIG. 2; SEQ ID.:2). Comparison of the sequence of the encoded peptide, referred to as rat intestinal trefoil factor (rITF), to the sequence of proteins in the Genebank database revealed significant homology to human breast cancer associated peptide (pS2; Jakowlev et al., 1984, Nucleic Acids Res. 12:2861) and porcine pancreatic spasmolytic peptide (PSP; Thim et al., 1985 Biochem. Biophys. Acta. 827:410). FIG. 3 illustrates the homology between rITf, PSP and pS2. Porcine pancreatic spasmolytic factor (PsP) and pS2 are both thought to fold into a characteristic structure referred to as a trefoil. A trefoil structure consists of three loops formed by three disulfide bonds. pS2 is thought to include one trefoil (FIG. 4A), and PSP is thought to include two trefoils (FIG. 4B). The region of rITF (nucleotide 114 to nucleotide 230 which encodes cys to phe), which is most similar to PSP and pS2, includes six cysteines all of which are in the same position as the cysteines which make up the trefoil in pS2 (FIG. 3). Five of these six cysteines are in the same position as the cysteines which form the amino terminal trefoil of PSP (FIG. 3). FIG. 5 depicts the proposed disulfide bond configuration of rITF.

Based on homology to PSP and pS2 (Mori et al., 1988, Biochem. Biophys. Res. Comm. 155:366; Jakowlew et al., 1984 Nucleic Acids Res. 12:2861), rITF includes a presumptive pro-sequence (met1 to ala22) in which 12 of 22 amino acids have hydrophobic side chains.

EXAMPLE 2

Production of Anti-rITF Antibodies

This example details how rat anti-ITF antibodies were generated.

A peptide corresponding to the carboxy-terminal 21 amino acids of rITF was synthesized and coupled to bovine serum albumin (BSA). This conjugate (and the unconjugated peptide) was used to raise polyclonal antibodies in rabbits. All procedures were standard protocols such as those described in Ausubel et al. (supra). The anti-rITF antibodies were used in an indirect immunoflouresce assay for visualization of rITF in rat tissues. Cryosections of rat tissues were prepared using standard techniques, and fluorescein labelled goat anti-rabbit monoclonal antibody (labelled antibodies are available from such suppliers Kirkegaard and Perry Laboratories, Gaithersberg, Md.; and Bioproducts for Science, Inc., Indianapolis, Ind.) was used to detect binding of rabbit anti-rITF antibodies. By this analysis rITF appears to be present in the globlet cells of the small intestine but not in the stomach or the pancreas.

EXAMPLE 3

Cloning of Human ITF

This example details how human ITF was cloned.

DNA encoding the rat ITF can be used to identify a cDNA clone encoding the human ITF (hITF). This can be accomplished by screening a human colon cDNA library with a probe derived from rITF or with a probe derived from part of the hITF gene. The latter probe can be obtained from a human colon or intestinal cDNA using the polymerase chain reaction to isolate a part of the hITF gene. This probe can then serve as a specific probe for the identification of clones encoding all of the hITF gene.

Construction of a cDNA Library

A human colon or intestinal cDNA library in λgtlO or λgtll, or some other suitable vector is useful for isolation of hITF. Such libraries may be purchased (Clontech Laboratories, Palo Alto, Calif. HLI034a, HLI0346b). Alternatively, a library can be produced using mucosal scrapings from human colon or intestine. Briefly, total RNA is isolated from the tissue essentially as described by Chirgwin et al. (1979, Biochemistry 18:5294; see also Ausubel et al., supra). An oligo (dT) column is then used to isolate poly(A)$^+$ RNA by the method of Aviv et al. (1972, J. Mol. Biol. 134:743; see also Ausubel et al., supra). Double-stranded cDNA is then produced by reverse transcription using oligo $(dT)_{12-18}$ or random hexamer primers (or both). RNAse H and E. coli DNA poll are then used to replace the RNA strand with a second DNA strand. In a subsequent step E. coli DNa ligase and T4 DNA polymerase are used to close gaps in the second DNA strand and create blunt ends. Generally, the cDNA created is next methylated with EcoRI methylase and EcoRI linkers are added (other linkers can be used depending on the vector to be used). In subsequent steps the excess linkers are removed by restriction digestion and the cDNA fragments are inserted into the desired vector. See Ausubel et al., supra and Sambrook et al. (1990, Molecular Cloning: A Laboratory Manual, Cold Spring Harbor Laboratory Press, Cold Spring Harbor, NY) for detailed protocols. Useful vectors include: λgtll, λgtlO, Lmabda ZAP®II vector, Lambda Uni-ZAP™ XR vector, all available from Stratagene (La Jolla, Calif.).

The cDNA library must be packaged into phage; this is most readily accomplished by use of a commercial in vitro packaging kit, e.g., Gigapack® II Gold or Gigapack®II Plus (Stratagene, La Jolla, Calif.). See Ausubel et al. (supra) for packaging protocols and suitable host strains. The library is preferably amplified soon after packaging; this step generates sufficient clones for multiple screening of the library. See Ausubel et al. supra or Sambrook et al. supra for details of amplification protocols and procedures for storing the amplified library.

Screening of the cDNA Library

To screen the library it must be placed on an appropriate host strain (e.g., Y1090 or Y1088 for λgtlO libraries, C600hflA for λgtlO libraries). After plating the phage, plaques are transferred to nitrocellulose or nylon filters (See Ausubel et al., supra and Sambrook et al. supra). The filters are then probed with $\alpha^{32}$P-labelled nick translated probe derived from rITF. The probe is preferentially generated using a portion of the region of rITF DNA coding for the trefoil structure (nucleotides 114 to 230 of SEQ ID NO.:1, which encodes cys32 to phe71 of SEQ ID NO.:2). This region is conserved between rITF, pS2 and PSP, and it is likely that this region is conserved between rITF and hITf. Once a plaque is identified, several cycles of plaque purification are required to isolate a pure clone encoding hITF. A phage DNA isolation is performed and the cDNA insert can be subcloned into an appropriate vector for restriction mapping and sequencing. If the phage vector is Lambda ZAP® II, coinfection with helper phage allows rescue and recircularization of pBluescript SK$^-$ phagemid vector (Stratagene, La Jolla, Calif.) harboring the cDNA; alternatively the phage clone is purified and the cDNA insert is subcloned into a vector suitable for restriction mapping and sequencing. If the clone does not contain the entire hITF gene (as assessed by homology to rITF and the presence of start and stop codons), the library can be rescreened with the original rITF probe or, preferably, with a probe generated from the hITF clone obtained. If none of the clones contain the intact gene, it can be reconstructed from clones which bear overlapping fragments of hITF.

Direct Isolation of an hITF Probe by PCR

It is possible to isolate part of the hITF gene directly from the packaged library or cDNa. To isolate a portion of hITf directly from the packaged library, a pair of oligonucleotide primers and Taq polymerase are used to amplify the DNA corresponding to the hITF gene. The primers used would be approximately 15–20 nucleotides long and correspond in sequence to the 5'-most and 3'-most portions of the rITf coding sequence. Friedman et al. (in PCR Protocols: A Guide to Methods and Applications, Innis et al., Eds., Academic Press, San Diego) describe a procedure for such amplification. Briefly, phage particles are disrupted by heating; Taq polymerase, primers (300 pmol of each), dNTPs, and Taq polymerase buffer are added; and the mixture is thermally cycled to amplify DNA. The amplified DNA is isolated by agarose gel electrophoresis. The ends of the fragment are prepared for ligation into an appropriate vector by making them flush with T4 polymerase and, if desired, adding linkers. Alternatively, a restriction site may be engineered into the fragment by using primers which have sequence added to their 5' ends which sequence will generate an appropriate sticky end when digested. For example the sequence: 5'-GGGCGGCCGC-3' (SEQ ID NO:5) can be added to the 5' end of each primer. This sequence includes the Noti restriction site flanked at the 5' end by the sequence: GG. The additional nucleotides prevent the 5' ends from denaturing and interfering with subsequent restriction digestion with NotI. The gel purified DNA of the appropriate size is next cloned into a cloning vector for sequencing and restriction mapping. This clone will not have the entire hITF sequence, rather it will be a combination of hITF (the region between the sequences corresponding to the primers) and rITF (the 5' and 3' ends which correspond to the primer sequences). However, this DNA can be used to generate a labelled probe (produced by nick translation or random primer labelling) which, since it is the correct hITF sequence, can be used in a high stringency screening of the library from which the cDNA was originally isolated. In an alternative approach, cDNA can be used in the above procedure instead of a packaged library. This eliminates the steps of modifying the cDNA for insertion into a vector as well as cDNA packaging and library amplification. Ausubel et al. supra provides a protocol for amplification of a particular DNA fragment directly from cDNA and a protocol for amplification from poly(A)$^+$ RNA.

Identification of a Presumptive Human ITF clone

A nick translated probe derived from rITF cDNA (corresponding to nucleotides 1 to 431 of SEQ ID NO.:1) was used for Northern blot analysis of poly(A)$^+$ RNA derived from human intestinal mucosal scrapings. Probe hybridization and blot washing were carried out according to standard procedures. Probe ($5\times10^5$ cpm/ml hybridization buffer) was hybridized to the filter at 45° C. in 5×SSC with 30% formamide. The filter was then washed at 60° C. in 5×SSC with 40% formamide. Using this protocol a band was clearly visible after an overnight exposure of the filter with an intensifying screen. This result indicated that there is sufficient homology between rITF and hITF to allow the use of probes derived from the sequence of the rITF gene for identification of the hITF gene.

A human intestinal cDNA library was obtained from Clontech (Palo Alto, Calif.). Alternatively, a human intestinal cDNA library may be produced from mucosal scrappings as described above. Four oligonucleotide probes were selected for screening the library cDNA. Two of the probes correspond to sequences within the region of rITF encoding the trefoil and are referred to as internal probes (5'GTACATTCTGTCTCTTGCAGA-3' (SEQ ID NO:6) and 5'-TAACCCTGCTGCTGCTGGTCCTGG-3' (SEQ ID NO:7)). The other two probes recognize sequences within rITF but outside of the trefoil encoding region and are referred to as external probes (5'-GTTTGCGTGCTGCCATGGAGA-3' (SEQ ID NO:8) and 5'-CCGCAATTAGAACAGCCTTGT-3' (SEQ ID NO:9)). These probes were tested for their utility by using them to screen the rat intestinal cDNA library described above. Each of the four probes could be used to identify a clone harboring all or part of the rITF gene. This result indicates that these probes may be used to screen the human intestinal library for the presence of hITF.

The internal probes were used as described above to amplify a DNA fragment from human colon library cDNA (Clontech, Palo Alto, Calif.). Linkers were added to the isolated DNA fragment which was then inserted into pBluescript phagemid vector (Stratagene, La Jolla, Calif.). The region of this clone corresponding to the sequence of human cDNA (i.e., not including the sequence corresponding to the internal probes) was used to make a radioactively labelled probe by random oligonucleotide-primed synthesis (Ausbel et al., supra). This probe was then used to screen the human colon cDNA library. This screening led to the identification of 29 clones. One of these clones (HuPCR-ITF) was nick-translated to generate a probe for Northern analysis of poly (A)$^+$ RNA isolated from human intestinal mucosal scrapings. A single band of roughly the same size as the rat transcript (approximately 0.45 kD) was observed.

Northern analysis of poly(A)$^+$ isolated from human tissues indicated that RNA corresponding to this probe was expressed in the small intestine and the large intestine but not in the stomach or the liver. These results indicate that the clone does not encode the human homolog of porcine PSP. Porcine PSP is expressed in porcine pancreas and is not significantly expressed in the small or large intestine. These results also distinguish the cloned gene from pS2 which is expressed in the stomach.

FIG. 6 shows the nucleic acid sequence information from the human ITF cDNa clone (SEQ ID NO:3), along with the deduced amino acid sequence in one-letter code (SEQ ID NO.:4). This clone was obtained in the experiment described above.

EXAMPLE 4

Human ITF

This example details recombinant production of human ITF, purification procedures for ITF, and procedures for generating antibodies against human ITF.

Production of hITf

The isolated hITF gene can be cloned into a mammalian expression vector for protein expression. Appropriate vectors include pMAMneo (Clontech, Palo Alto, Calif.) which provides a RSV-LTR enhancer linked to a dexamethasone-inducible MMTV-LTR promoter, an SV40 origin of replication (allows replication in COS cells), a neomycin gene, and SV40 splicing and polyadenylation sites. This vector can be used to express the protein in COS cells, CHO cells, or mouse fibroblasts. The gene may also be cloned into a vector for expression in drosphilia cells using the bacoluvirus expression system.

Purification of ITF

ITF can be purified from intestinal mucosal scrapings of human, rats or any other species which expresses ITF (pigs and cows may provide a source of ITF). The purification procedure used for PSP will be useful for the purification of ITF since the proteins are likely to be homologous. Jorgensen et al. describes a method for purification of PSP (1982, Regulatory Peptides 3:207). The preferred method is the second approach described by Jorgensen et al. (supra). This method involves chromatography of SP-Sephadex C-25 and QAE Sephadex A-25 columns (Sigma, St. Louis, Mo.) in acidic buffer.

Anti-ITF Monoclonal Antibodies

Anti-ITl monoclonal antibodies can be raised against synthetic peptides whose sequences are based on the deduced amino acid sequence of cloned hITF (SEQ ID NO.:4). Most commonly the peptide is based on the amino- or carboxy-terminal 10–20 amino acids of the protein of interest (here, hITF). The peptide is usually chemically cross-linked to a carrier molecule such as bovine serum albumin or keyhole limpet hemocyanin. The peptide is selected with the goal of generating antibodies which will cross-react with the native hITf. Accordingly, the peptide should correspond to an antigenic region of the peptide of interest. This is accomplished by choosing a region of the protein which is (1) surface exposed, e.g., a hydrophobic region or (2) relatively flexible, e.g., a loop region or a β-turn region. In any case, if the peptide is to be coupled to a carrier, it must have an amino acid with a side chain capable of participating in the coupling reaction. See Hopp et al. (1983, Mol. Immunol. 20:483; 1982, J. Mol. Biol. 157:105) for a discussion of the issues involved in the selection of antigenic peptides. A second consideration is the presence of a protein homologous to hITF in the animal to be immunized. If such a protein exists, it is important to select a region of hITF which is not highly homologous to that homolog.

For hITf, peptides that correspond to the amino-terminal or carboxy-terminal 15 amino acids are likely to be less homologous across species and exposed to the surface (and thus antigenic). Thus they are preferred for the production of monoclonal antibodies. Purified hITF can also be used for the generation of antibodies.

EXAMPLE 5

Genetic Disruption of a Trefoil Protein Impairs the Defense of Intestinal Mucosa This example details disruption of the mouse endogenous ITF gene and the phenotype of the ITF deficient mouse.

Isolation of the Murine ITF Gene and Generation of ITF-Deficient Mice

The murine ITF gene was isolated from a phage genomic library using the rat ITF cDNA sequence as a probe, and its identity was confirmed by nucleotide sequencing using standard techniques (Mashimo et al., 1995, Biochem. Biophys. Res. Comm. 210:31).

Figure 7:
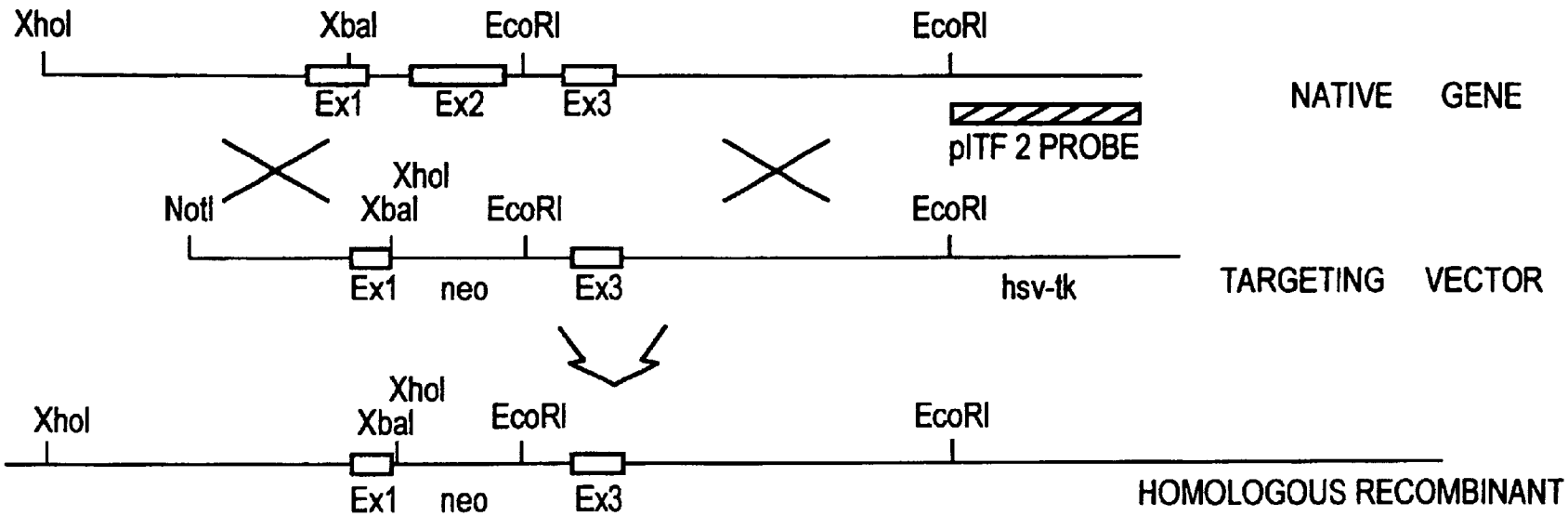
FIG. 7 is a diagram depicting the strategy used to mutate the ITF gene in embryonic stem cells.

A targeting vector for disrupting the gene by homologous recombination in embryonic stem (ES) cells was designed and constructed, as shown in FIG. 7. The entire second exon (Ex2) of the murine ITF gene, which is contained within the XbaI-EcoRI fragment shown, was replaced with the neomycin resistance (neo) gene cassette. As the deleted sequence encodes most of the "trefoil domain", the ability of any resultant peptides to produce the looping structure characteristic of trefoil proteins is abolished. A positive-negative selection strategy (Mansour et al., 1988, Nature 336:348) was used to enrich for homologous recombination events in the embryonic stem (ES) cells by selecting the neo within the homologous DNA and against a herpes simplex virus thymidine kinase gene (hsv-tk) placed at the 3' end of the targeting vector. The pPNT plasmid (Tybulewicz et al., 1991, Cell 65:1153) was used to construct the targeting vector. The targeting vector was linearized with the restriction enzyme NotI and electroporated into pluripotent J1 ES cells (Li et al., 1991, Cell 69:915) under conditions previously described (Strittmatter et al., 1995, Cell 80:445). Disruption of the ITF gene in ES cells following homologous recombination was distinguished from random integration of the targeting vector by Southern blot analysis of genomic DNA from individual clones of cells digested with the restriction enzyme XhoI. The pITF2 probe identified a 19 kb "wild type" fragment and a 23 kb "knock out" fragment created by introduction of an XhoI site upon homologous insertion of the targeting vector. Approximately 10% of neomycin-resistant ES clones were found to have undergone homologous ITF recombination using this method.

The polymerase chain reaction (PCR) was used to confirm the targeted mutation as follows. A 200 bp region of DNA was amplified using primers spanning exon 2 of ITF (5'-GCAGTGTAACAACCGTGGTTGCTGC-3' (SEQ ID NO.:10) and 5'-TGACCCTGTGTCATCACCCTGGC-3' (SEQ ID NO.:17)); and a 400 bp region of the neo gene was amplified with a second set of primers (5'-CGGCTGCTCTGATGGCCGCC-3' (SEQ ID NO.:18) and 5'-GCCGGCCACAGTCGATGAATC-3' (SEQ ID NO.:19)). The DNA template for the PCR reaction was obtained from tail tissue. Approximately 0.5 cm of the tail was cut off each animal, and the samples were digested with proteinase-K (200 μl at 0.5 mg/ml in 50 mM Tris-HCl pH 8.0 and 0.5% Triton X-100; Sigma, St. Louis, Mo.) at 55 EC overnight. One μl of this mixture was added directly to a 25 μl PCR reaction (per Stratagene, Menosha, Wis.). The reaction was begun with a "hot start" (incubation at 96° C. for 10 minutes), and the following cycle was repeated 30 times; 72° C. for 120 seconds (hybridization and elongation) and 96° C. for 30 seconds (denaturation). Ten μl of each reaction mixture was electrophoresed on a 2% agarose gel. Wild type animals were identified by the presence of a 200 bp fragment, corresponding to an intact ITF gene, heterozygous animals were identified by the presence of this band and, in addition, a 400 bp fragment produced by amplification of the neo gene, and ITF-deficient (knock out) animals were identified by the presence of only the fragment corresponding to the neo gene.

Two ES clones, which arose independently, were used to derive two lines of mice lacking ITF. These mice were screened by Southern genomic blot analysis as described for ES clones, or by PCR.

Analysis of Trefoil Peptide Expression in Wild Type and Mutant Mice

Although expression of ITF is abolished in the mutant mice, expression of other trefoil genes is preserved. Northern blot analysis was performed using cDNA probes for ITF (Suemori et al., 1991. Proc. Natl. Acad. Sci. USA 88:11017), SP (Jeffrey et al., 1984 Gastroenterology 106:336), and, as a positive control, glyceraldehyde 3-phosphate dehydrogenase (GAPDH). The nucleic acid probe for murine pS2 was made by reverse transcription-polymerase chain reaction (RT-PCR) Lsing the oligonucletoide pairs: 5'-GAGAGGTTGCTGTTTTGATGACA-3' (SEQ ID NO.:20) and 5'-GCCAAGTCTTGATGTAGCCAGTT-3" (SEQ ID NO.:21), which were synthesized based on the published mouse pS2 cDNA sequence (GenBank Accession Number: Z21858). The GenAmp RNA PCR Kit (Perkin Elmer) was used according to the manufacturer's instructions, as was the pCRJII (Invitrogen) cloning vector. RNA was extracted from the following tissues from both wild type and ITF-deficient (knock out) mice: stomach, duodenum, terminal ileum, right colon, appendix, transverse colon, left colon, and rectum. Fifteen μg of total RNA from each sample were electrophoresed on a 1% agarose gel, and transferred to nitrocellulose paper. Following hybridization, washing, and autoradiography, wild type mice exhibited a pattern of tissue expression considered normal: ITF was expressed in the small intestine and colon, which is the same expression pattern seen for ITF in the rat and human. The analysis of mutant mice confirmed the lack of ITF expression in the gastrointestinal tract. In contrast, the expression of the order trefoil proteins, SP and pS2, are unaltered in the gastrointestinal tract of mutant mice. SP was expressed in the stomach and, at lower levels, in the duodenum of both wild type and mutant mice. Similarly, pS2 was expressed in the stomach of both wild type and ITF-deficient mice.

Immunocytochemistry Reveals that ITF is not Expressed in the Colon of ITF-deficient mice In order to confirm that ITF protein was not expressed by ITF knock out mice, immunocytochemistry was performed as follows. Tissue from the colon and small intestine was fixed in the course of perfusion, immersed in 4% paraformaldehyde (McLean et al., 1974, J. Histochem. Cytochem. 22:1077), and embedded in paraffin. Sections were collected and stained either with a polyclonal antibody raised against a synthetic peptide from the predicted 18 carboxy-terminal amino acids of murine ITF or a monoclonal antibody against colonic mucin (Podolsky et al., 1986, J. Clin. Invest. 77:1263). Primary antibody binding was visualized with a biotinylated secondary antibody, Avidin DH, biotinylated horseradish peroxidase H, and diaminobenzidine tetrahydrochloride reagents according to the manufacturer's instructions (VectaStain ABC, Vector Laboratories, Bulingame, Calif.). Following immunocytochemistry, the sections were counterstained with hematoxylin and viewed. Goblet cells in the colon of wild type mice were immunoreactive with both antibodies, staining positively for ITF and mucin. In contrast, the goblet cells in the colon of ITF-deficient mice lacked detectable ITF but continued to express colonic mucin.

Induction of Mild Colonic Epithelial Injury with Dextran Sulfate Sodium

ITF-deficient mice derived from each ES clone appear to develop normally and are grossly indistinguishable from heterozygous and wild type litter mates. Their growth is not retarded and they reach maturity without evident diarrhea or occult fecal blood loss. However, the colon of ITF-deficient mice may be more prone to injury than the colon of wild type mice. To investigate this hypothesis, dextran sulfate sodium (DSS), which reproducibly creates mild colonic epithelial injury with ulceration in mice (Kim et al., 1992, Scand. J. Gastroent. 27:529; Wells et al., 1990, J. Acquired Immune Deficiency Syndrome 3:361; Okayasu et al., 1990, Gastroenterology 98:694) was administered in the animal's drinking water. After standardization of DSS effects in comparable wild type mice, a group of 20 wild type and 20 ITF-deficient mice (litter mates from heterozygous crosses, weighing >20 grams each) were treated with 2.5% DSS in their drinking water for nine days.

Figure 8:
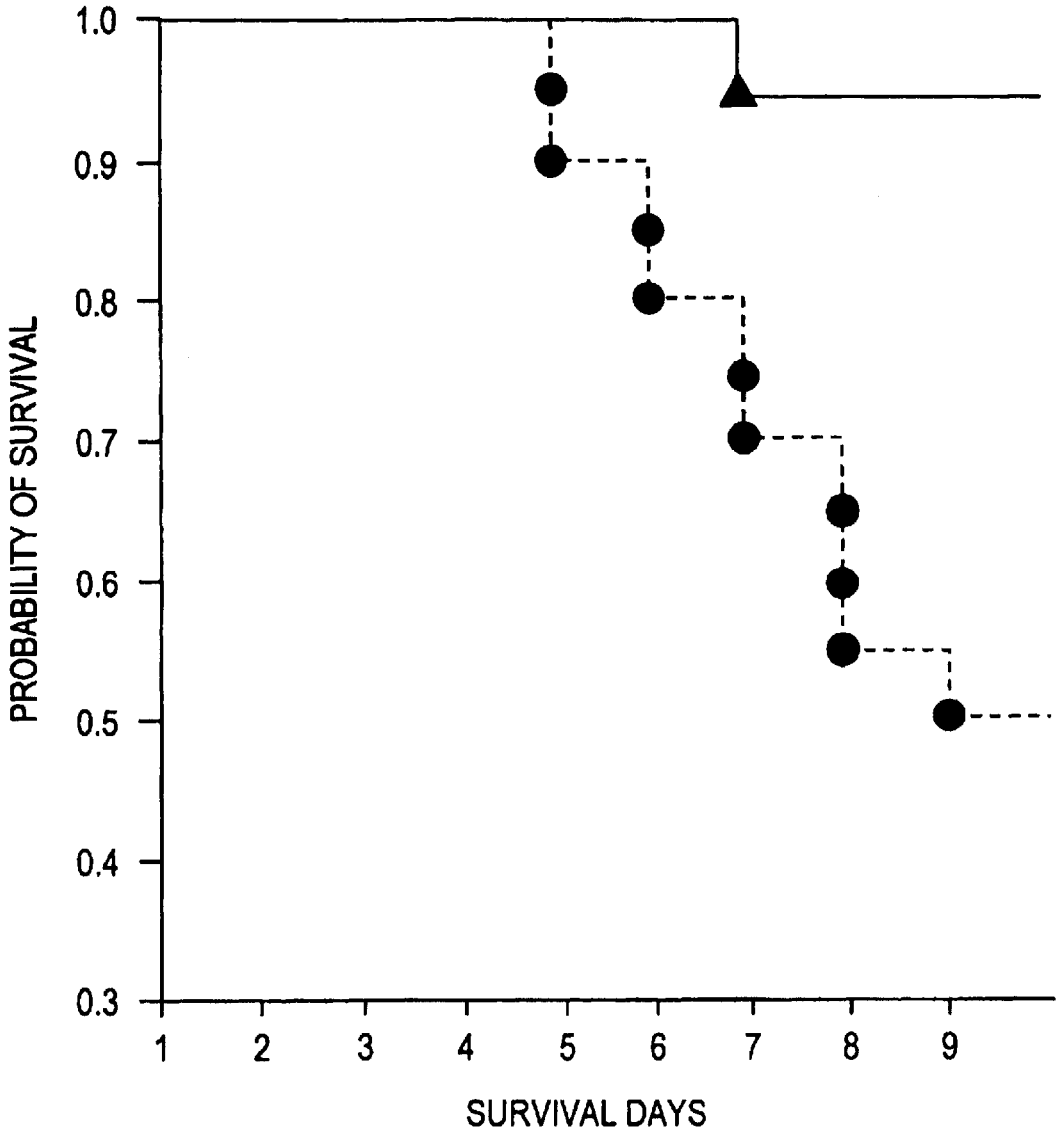
FIG. 8 is a graph depicting survival following administration of Dextran Sulfate Sodium (DSS; 2.5% w/v in drinking water for 9 consecutive days), shown as Kaplan-Meier transform of probability versus days of DSS treatment.

Although 85% of wild type mice and 100% of ITF-deficient mice treated with DSS demonstrate occult blood (using Hemoccult, Smith Kline Diagnostics, San Jose, Calif.) in their stool during the period of treatment, ITF-deficient mice were markedly more sensitive to the injurious effects of DSS. Fifty percent of ITF-deficient mice developed frankly bloody diarrhea and died (FIG. 8). In contrast, only 10% of wild type mice treated similarly exhibited bloody diarrhea, and only 5% died. Weight loss was also significantly more pronounced in ITF-deficient mice than wild type mice receiving DSS.

ITF-Deficient Mice Treated with Dextran Sulfate Sodium (DSS) Develop Severe Colonic Erosions After seven days of treatment with DSS (2.5% w/v), the colons of wild type and ITF-deficient mice were examined histologically. Left colon transections were fixed in 4% paraformaldehyde, mounted in paraffin, and stained with hematoxylin and eosin. Multiple sites of obvious ulceration and hemorrhage were present in the colon of ITF-deficient mice, while the colons of most wild type mice were grossly indistinguishable from those of untreated mice. Histological examination of the DSS-treated ITF-deficient colon confirmed the presence of multiple erosions and intense inflammatory changes including crypt abscesses. Damage was more pronounced in the distal colon, i.e., the descending colon, sigmoid colon, and rectum, which contained large, broad areas of mucosal ulceration. When similarly inspected, mucosal erosions could be seen in the tissue of 80% of the DSS-treated wild type mice, but most were small lesions that also appeared to be healing, with complete re-epithelialization of most lesions. There was no evidence of re-epithelialization in the colons of ITF-deficient mice exposed to DSS.

During the normal course of growth and development, intestinal epithelial cells originate from stem cells in the intestinal crypts and rapidly progress up the crypt and villus to be extruded from the villus tip within the five days. After intestinal injury, the epithelial covering is repopulated by cells which appear to generate signals to heal the lesion by modulation of epithelial and mensenchymal cell growth and matrix formation (Poulson et al., 1993, J. Clin. Gastroenterol. 17:S78). In vitro evidence suggests that trefoil proteins play a key role in re-establishing mucosal integrity after injury. Despite the normal restriction of SP and pS2 expression to the proximal gastrointestinal tract, these trefoil proteins and ITF are abundantly expressed at sites of colonic injury and repair.

The DSS model described above provides a system for testing the protective effects of ITF, other trefoil peptides, or active polypeptide fragments or variants thereof. One can administer a molecule to be tested to DSS-treated mice, either wild type or ITF-deficient mice, and determine whether the molecule has therapeutic effects by performing the assays described above.

In addition to the use of DSS, any chemical compound that is known to damage the mucosa lining the digestive tract can be used to assay the proteins of the invention. These compounds include, but are not limited to, alcohol, indomethacin, and methotraxate. For example, methotrexate (MTX) can be administered intraperiotoneally to mice at a dose of 40 mg/kg. One group of MTX-treated animals could be given, in addition, the protein in question. Various parameters, such as body weight, the presence of lesions in the digestive tract, and mortality of these animals could then be compared to equivalent measurements taken from animals that were not treated with the protein.

Anti-apoptotic effect of ITF

ITF knock-out mice were generated as described above. Analysis of colonic crypts for apoptotic colonic epithelial cells revealed that more apoptotic colonic epithelial cells were observed in the colonic crypts of the ITF knockout mice than in the wild type mice.

EXAMPLE 6

In situ H. plyori Binding Assay

This example describes a method for determining whether ITF (or protein fragment or variant thereof) prevents or can be used to treat diseases associated with H. plyori infection.

In order to determine if ITF is useful as a protein that can prevent or treat diseases associated with H. plyori infection, an established animal method of H. plyori infection can be used. One such model was recently developed by Falk et al. (1995, Proc. Natl. Acad. Sci. USA 92:1515–1519). This model involves the use of transgenic mice that express the enzyme α-1,3/4-fucosyltransferase and, as a consequence, express $Le^b$ on the surface of mucosal cells that bound clinical isolates of H. plyori. If the addition of a protein, such as ITF, to this system reduces the level of H. plyori binding to the mucosal cell, the protein would be considered an inhibitor of H. plyori. More specifically, the assay could be carried out as follows. H. plyori are obtained, for example, from patients with gastric ulcers or chronic active gastritis, grown to stationary phase, and labeled, for example with digoxigenin or fluorescein isothiocyanate (FITC). The labeled bacteria are then exposed, together with the protein of interest, to frozen sections prepared from the stomach, duodenum, ileum, or liver of adult transgenic mice (as described above). As a control, the experiment could be performed in parallel using tissue from a wild type litter-mate. The sections are fixed with ice-cold methanol for 5 minutes, rinsed three times with wash buffer (TBS; 0.1 mM $CaCl_2$, 1 mM $MnCl_2$, 1 mM $MgCl_2$; 10 minutes/cycle), and treated with blocking buffer (Boehringer Mannheim; see also Falk supra). Bacteria are diluted to an $OD_{600}$ of 0.05 with dilution buffer [TBS; 0.1 mM $CaCl_2$, 1 mM $MnCl_2$; 1 mM $MgCl_2$ containing leupeptin (1 μg/ml), aproptinin (1 μg/ml), [-1-p-tosylamido-2-phenylethyl chloromethyl ketone (100 μg/ml), phenylmethylsulfonyl fluoride (100 μg/ml), and pepstatin A (1 μg/ml)] and overlaid on the sections for 2 hours at room temperature in a humidified chamber. Slides are then washed six times in wash buffer on a rotating platform (5 minutes/cycle at room temperature). Digoxigenin-labeled bacteria are visualized on washed slides with FITC-conjugated sheep anti-digoxigenin immunoglobulin (Boehringer Mannheim) diluted 1:100 in histoblocking buffer. Nuclei were stained with bisbenzimide (Sigma). For blocking controls, digoxigenin-conjugated stationary-phase bacteria can be suspended in dilution buffer to an $OD_{600}$ of 0.05 and shaken with or without $Le^b$-HSA or $Le^a$-HSA (final concetration, 50 μg/ml; reaction mixture, 200 μl) for 1 hour at room temperature. The suspension is then overlaid on methanol-mixed frozen sections.

EXAMPLE 7

Mutants of ITF

This example describes the generation of ITF mutants and the determination of which residues are critical for the biological function of ITF. Biological functions of ITF include cell migration, EGF receptor phosphorylation and anti-apoptotic effects.

ITF has a unique three loop structure which is formed by intrachain disulfide bonds between six cysteine residues. These six cysteine residues were mutated in turn to serine residues thereby generating six mutants which have incomplete tertiary loop structure. The mutants were generated using site-directed mutagenesis of the ITF cDNA sequence.

A "non-dimerized" mutant of ITF was generated by converting the seventh cysteine residue to a serine. The seventh cysteine residue is located near the carboxy terminus of the protein which is thought to permit homodimer formation.

A C-terminal truncated ITF was generated by removing the 10 C-terminal amino acids (truncated after the 6th cysteine).

EXAMPLE 8

Protease Resistance of ITF

This example details the effect of different proteases on wild-type ITF and mutant ITF.

10 microgram of mutant ITF proteins were incubated with 0.0, 0.01, 0.1, 1.0 and 10.0 microgram of trypsin or 0.0, 0.01, 0.1, 1.0 and 10.0 microgram of pepsin for 4 hours and electrophoresed on the PAGE gels. The amount of digested and undigested protein was measured. Results showed that mutated and C-terminal truncated ITF-fusion proteins were significantly more easily digested by the proteases than wild type ITF protein.

EXAMPLE 9

Promotion of Cell Migration by Mutant ITF

This example details an experiment for determining if the mutant ITF can cause migration of cells.

The mutant ITF proteins were added to cultured colonic epithelial cells (IEC-6) and subjected to a cell migration assay. Briefly, a confluent monolayer of cultured IEC-6 cells was wounded by a razor blade and then incubated with wild-type and mutant ITF for 24 hours. The number of migrating cells across the wounded edge was then counted. The seven mutated ITF proteins showed a decrease in migration activity of 40 to 60% as compared to the wild type ITF protein. The C-terminal truncated ITF protein showed no migration activity. Thus, for epithelial cell migration, the C-terminal portion as well as the trefoil motif of ITF is important.

EXAMPLE 10

Phosphorylation of EGF Reactor by ITF Mutants

The ability of the fusion proteins to phosphorylate the epidermal growth factor receptor was determined. HT29 cells were stimulated by the addition of 100 microgram/ml of an ITF proteins for 5 minutes and lysed. Each cell lysate was immunoprecipitated by the anti-human EGFR antibody (4G10) and immunoblotted. Phosphorylation of the EGF receptor was only detected when wild-type ITF protein was added to the cells. This result suggests that tyrosine phosphorylation of EGF receptor requires the complete structure of the ITF peptide.

EXAMPLE 11

Anti-anoptotic Effect of ITF Mutants

The anti-apoptotic effect of the ITF mutant proteins was investigated by measuring apoptosis following etoposide-induced apoptosis in cultured cells.

HCT116 cells were preincubated with 3 mg of ITF protein or BSA overnight and then further incubated for 24 hours with 1 mM of etoposide. Cells lysates were electrophoresed on the SDS-PAGE and subjected to western blotting using anti-Poly (ADP-ribose) polymerase (PARP) antibody. Apoptosis-related cleavage fragments were detected in cells which were incubated with mutated ITF protein. In contrast, no apoptosis cleavage fragments were detected for HCT116 which were treated with wild-type ITF. This result suggests that the anti-apoptotic effect of ITF requires the complete structure of ITF, including the trefoil motif.

EXAMPLE 12

ITF Promotes Eye Wound Healing

This example describes experiments that were undertaken to determine if ITF has a role in eye wound healing. The experiments involved isolating and culturing primary rabbit corneal epithelial cells, wounding the cells, and then performing a migration or restitution assay. In addition further experiments were performed to compare the effect of trefoil proteins and other known growth factors such as TGF on wound healing.

Isolation and culture of primary rabbit corneal epithelial cells

Primary corneal epithelial cells were isolated from New Zealand rabbits (2.5 kg). In brief, 9 mm discs were removed by trypsinization, stroma was separated from the overlying epithelium and underlying endothelium and cells were passaged. Fibroblasts were removed by scalpel and remaining corneal epithelial cells seeded onto 12-well (restitution assay) or 24-well plates (proliferation assay). Cells were cultured in 4.5 g/l glucose containing Dulbecco's modified Eagle medium, (DMEM, Cellgro, Mediatech Inc., Herndon, Va.) containing 4 mM L-glutamine, 100 I.U/ml penicillin/

100 μg/ml streptomycin, and 10% heat-inactivated FBS (fetal bovine serum, Sigma Chemical Co., St. Louis, Mo.). Mitomycin C (Sigma Chemical Co.) was added to the serum-starved monolayers for 2 hours before starting the restitution assay described above to inhibit cell proliferation and was used at concentrations of 1 μg/ml.

In vitro corneal epithelial cell migration/restitution assay

Primary rabbit corneal epithelial wound assays were performed by modification of techniques described for intestinal epithelial cells. Cells were grown to confluency, then washed and cultured in serum-deprived (0.1% FBS containing) medium for 12 hours. Monolayers were then wounded with a sterile blade (3–5 wounds of 5–7 mm length per dish/wound area) and subsequently stimulated with increasing doses of the purified recombinant trefoil peptide SP which is normally predominantly expressed in the proximal gastrointestinal tract, or recombinant human ITF (hITF) which is expressed in the small and large intestine. Effects of trefoil peptides were evaluated over a range of concentrations from 0.1 to 1 μg/μl.

Trefoil peptides, hITF and hSP, were observed to cause a substantially enhanced number of cells to migrate over the original wound edge 12 hours after wounding of the corneal epithelial monolayers. Since proliferation of confluent serum-starved monolayers of primary corneal epithelial cells was very low, the number of cells counted over the original wound scratch mark after 12 hours represents cell migration but does not reflect cell proliferation. This result is consistent with previous observations in an in vitro restitution model using intestinal epithelial cells.

Assessment of the functional role of trefoil peptides on corneal epithelial restitution.

Wound areas were viewed under the microscope and wound margins labelled with a marker to avoid later observer bias. After washing, wounded corneal epithelial monolayers were cultured in serum-deprived medium in the presence or absence of hSP (0.1–1 μg/μl), hITF (0.1–1 μg/μl), TGF-α (100 ng/ml), TGF-$\beta_1$ (5 ng/ml). BSA (1 μg/μl) was used as non-specific control protein. Anti-TGF-α and anti-TGF-β antibodies and normal rabbit IgG control were used at a concentration of 10 μg/ml. After 12 hours, cell culture medium was aspirated and cells were fixed with a 2% glutaraldehyde/PBS$^+$ solution. Cell migration was assessed in a blinded fashion by counting cells found across the former wound margin. The previously labelled standardized wound areas were photographed at 100-fold magnification using an inverted Nikon Diphaor TMS microscope (Nikon Inc., Melville, N.Y.). Migration studies were performed in triplicate, and at least 3 wound areas per plate were analyzed for cell migration.

Figure 11:
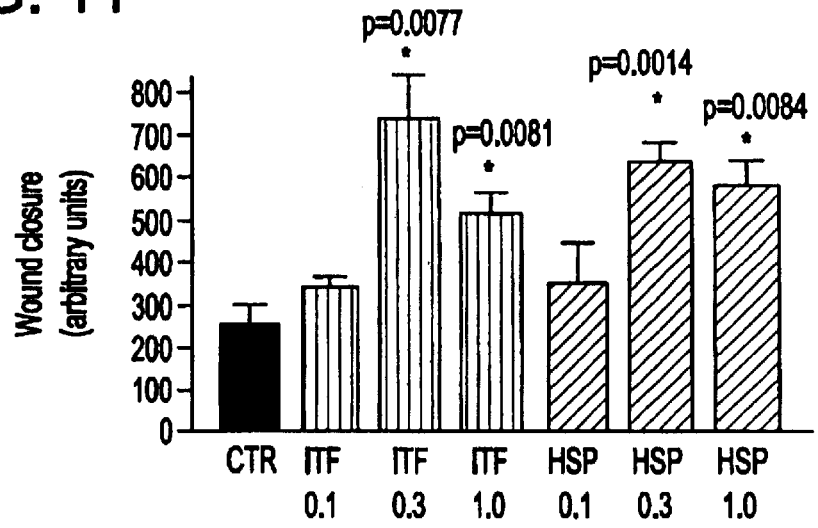
FIG. 11 is a graph depicting dose-dependent effects of the trefoil peptides ITF and hSP on corneal epithelial migration. Values are mean±SEM.

The restitution enhancing effects of both, hITF and hSP on wounded corneal epithelial cells were dose-dependent as shown in FIG. 11. For both trefoil peptides, restitution promoting effects compared to medium containing control protein BSA were most pronounced at a final concentration of 0.3 μg/μl.

Figure 12:
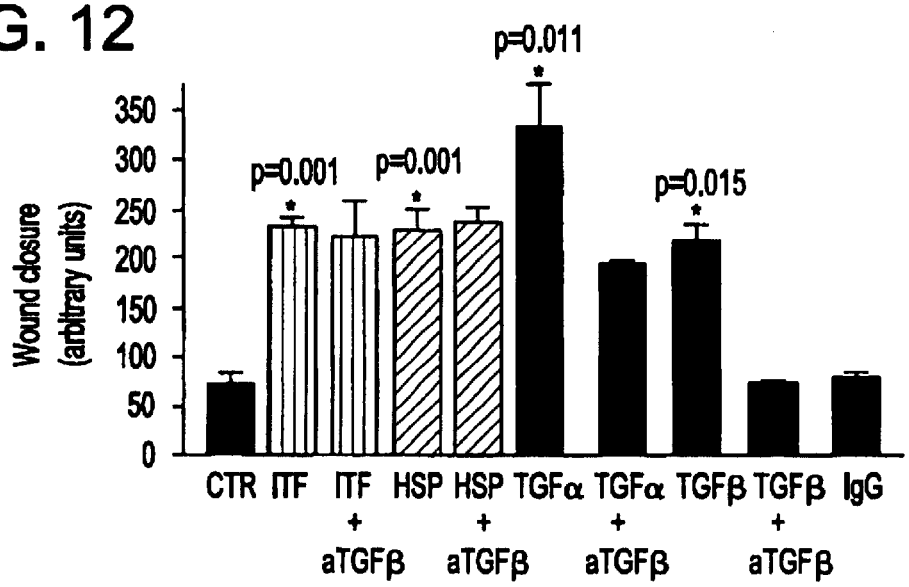
FIG. 12 is a graph depicting the effects of neutralizing anti-TGF-$\beta_1$-antibody on ITF and hSP stimulated corneal epithelial restitution. Values are mean±SEM.

Since it is known that peptide growth factors promote migration of corneal as well as intestinal epithelial cells, the effects of trefoil factors hITF and hSP were compared to effects of TGF-α and TGF-$\beta_1$. As demonstrated in FIG. 12, addition of 100 mg/ml TGF-α to wounded corneal epithelial monolayers resulted in a five-fold increase in restitution compared to control medium (p=0.011), whereas addition of TGF-$\beta_1$ at a concentration of 5 ng/ml effected a four-fold increased migration rate (p=0.015). The restitution enhancing effects of both TGF-$\beta_1$ and of TGF-α were substantially inhibited by addition of neutralizing anti-TGF-β-antibody suggesting that TGFβ is necessary or part of a final common pathway through which diverse peptide growth factors and cytokines promote restitution. The magnitude of the observed restitution promotion effects of trefoil peptides was comparable to the effects of TGF-$\beta_1$. However, the effects of hITF and hSP on corneal epithelial restitution were not significantly affected by addition of neutralizing anti-TGF-β-antibody.

Mitogenic assays

Figure 13:
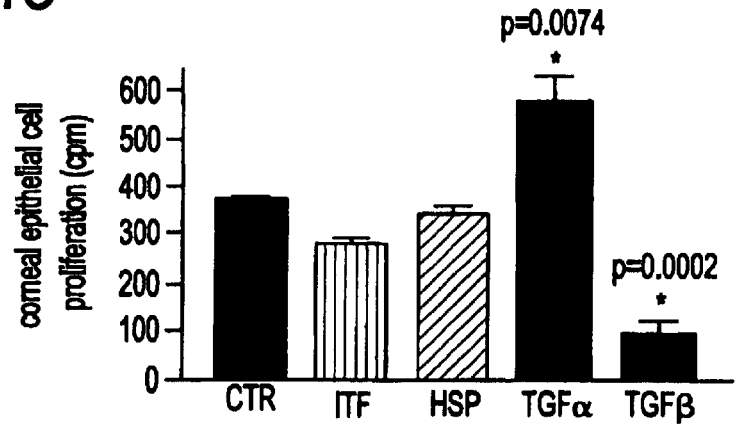
FIG. 13 is a graph depicting the effects of trefoil peptides on proliferation of primary rabbit corneal epithelial cells. Values are mean±SEM.

Primary rabbit corneal epithelial cells were seeded into 24-well plates ($1–5\times10^4$/well) in DMEM containing 10% FBS. When cells were approximately 50% confluent, cells were washed and cultured for 18 hours in medium containing 0.1% FBS. Cells were then cultured in 0.1% FBS containing medium in the presence or absence of trefoil peptides, growth factors, neutralizing antibodies, control protein or IgG. After 20 hours, [$^3$H]thymidine was added (1.8 μCi well of 24 well plate). After 4 hours, the incorporation of radiolabeled thymidine was determined (Ciacci, Gastro93). Briefly, cells were washed with PBS and fixed with methanol-acetic acid (3:1, v/v). Acid-insoluble material was then lysed with NaOH, and radioactivity was counted using a liquid scintillation counter. Results as shown in FIG. 13 showed that the stimulation of subconfluent primary corneal epithelial cells with hITF resulted in a somewhat lower [$^3$H]-thymidine incorporation (291±12 cpm) compared to the effects of control medium (373±4 cpm), a difference which was not significant. In addition, hSP also did not significantly affect corneal epithelial proliferation (344±17 cpm). In contrast addition of TGF-α (589±45 cpm; p=0.0074) significantly enhanced and TGF-β (95.3±23 cpm; p=0.002) significantly decreased proliferation of cornal epithelial cells.

EXAMPLE 13

In vivo Eye Wound Treatment Assay

Animal models can be used to evaluate the in vivo efficacy of treatment of ITF or other trefoil proteins on corneal epithelial wound healing. Corneal wounding can be inflicted using mechanical force (Steibel-Kalish et al., Eye, 1998, 12:829–333; Reidy et al. British Journal of Ophthalmolgy, 1994, 78:377–380; and Xie et al., Australian and New Zealand Journal of ophthalmolgy, 1998, 26:47–49), exposure to an alkali (Perry et al., Cornea, 12:379–382, 1993), or exposure to iodine vapours (Rieck et al., Exp. Eye Res. 54, 987–998, 1992).

In addition, the role of trefoil as a protector against virus or bacterial invasion can be determined in vivo, e.g., using a murine model of herpes simplex virus type 1 (Brandt et al. Antimicrobial agents and chemotherapy, 1078–1084, 1996).

Rabbit mechanical trauma model

Cornal wounding can be inflicted using mechanical trauma (Crosson et al., Ophthalmol Vis Sci, 1986; 27:464–73). Briefly, an artificial, controlled wound of identical size and depth is inflicted to the corneas of a group of rabbit eyes in order to measure their healing rates. The controlled wound is inflicted using a 7.12 mm rotating disc which causes an identical epithelial defect (surface area 40 mm$^2$, depth 40 um). The depth of the wound is controlled by an adjustment knob on the rotating disc. After wound infliction, a trefoil protein can be administered topically. For topical administration, the right rabbit eye is treated with a trefoil protein (e.g., ITF or PS) and the left eye is untreated and serves as a control. Timing of the treatment is planned so that during the acute phase of healing (first 48 hours) medication is administered as often as six times daily.

The rabbits eyes are examined at 8 hour intervals by slit-lamp microscopy and color photographs taken. Before each examination the rabbits are anesthetized and their corneas stained with 2% fluorescein solution. The photographs are projected from a fixed distance onto a millimetric grid scale and the area of erosion that has closed is measured in square magnification. The photographs were taken at the same magnification (×100) throughout the study.

After complete re-epithelization the rabbits are killed, eyes fixed and stained with haematoxylin-eosin for microscopic examination of the corneal epithelium.

Rabbit alkali-burn model

Alternatively, corneal wounding can be caused by chemicals, e.g., Sodium hydroxide. Briefly, a circular plastic well with an 11-mm inner diameter is sequentially placed on the eyes of all rabbits and filed with 0.5 ml of 1N sodium hydroxide (Levinson et al., Invest Ophthalmol Vis Sci, 1976:15:986–93). After 30 seconds the alkali was removed by hypodermic syringe, and the eye was rinsed for 5 seconds with normal saline solution. Trefoil can be administered topically. For topical administration, the right eye of the rabbit serves as a control while the left eye receives treatment with trefoil. As described above, eyes are examined for epithelial healing.

Rabbit iodine-vapor model

Both eyes of each rabbit are wounded following exposure to iodine (Moses et al. Invest. Ophthal mol. Vis. Sci. 1979, 18:103–106). Briefly, iodine vapours from a glass cylinder (internal diameter of 7.4 mm) containing iodine crystals are applied to the corneal epithelium. Following exposure to iodine the right eye of each animal receives topical application of trefoil and the left eye is the control eye and receives no treatment. Treatment of trefoil is applied once or more times daily.

Wound healing was determined as above.

Murine Model of Herpes Simplex virus type 1 (HSV-1)

To determine the effect of trefoil on Herpes Simplex virus type 1 occular disease the right and left cornea of a mouse is scratched three times vertically or three times horizontally with a sterile 30-gauge needle. A drop of DMEM containing approximately $10^6$ PFU of HSV-1 is placed on the left damaged cornea and left for 30 seconds. Excess inoculum is removed by adsorption with a sterile swab.

The mice are treated topically once or more times a day with trefoil protein. Briefly, mice are anesthetized by inhalation halothane and trefoil is applied with sterile micropipette tip to cover of cornea.

On days 1, 2, 3 6 or 10 the amount of infectious virus is determined by plague assay on vero cell monolayers.

Use

In the practice of the present invention, ITF may be administered orally, intravenously, or intraperitoneally for treatment of peptic ulcer diseases, inflammatory bowel diseases, eye disorders, for protection of the intestinal tract from injury caused by bacterial infection, radiation injury or other insults, for promoting healing of corneal tissue or preventing wounding of corneal tissue. The mode of administration, dosage, and formulation of ITF will depend upon the condition being treated.

Skilled pharmacologists are able to readily determine appropriate dosage requirements. As trefoil peptides are not degraded within the digestive tract, it is expected that the route of administration will be oral for treating disorders of the digestive tract. However, trefoil proteins can be administered topically for treatment of eye disorders. The dosage will range from 1 to 500 mg, taken once to three times per day. The peptide could be administered, for example, in the form of a tablet, capsule, cream, or pill, or could be suspended in a solution, such as a syrup, that the pateint swallows. Alternatively, the solution containing the peptide may be administered as a gastric lavage. The peptide may also be included in a solution that is administered as an enema, or it may be administered as a suppository. ITF or pS2 can be administered as a monomer or can be administered as a dimer.

Other Embodiments

ITF may be used to produce monoclonal antibodies for the detection of ITF in intestinal or blood serum by means of an indirect immunoassay. ITF may be detectably labelled and used in an in situ hybridization assay for the detection of ITF binding sites. Labels may include, but are not limited to, fluorescein or a radioactive ligand.

ITF may be used to protect and stabilize other proteins. This protection is accomplished by forming a hybrid molecule in which all or part of ITF is fused to either the carboxy-terminus or the amino-terminus (or both) of the protein of interest. Because ITF is resistant to degradation in the digestive system, it will protect the protein of interest from such degradation. As a consequence, the protein of interest is likely to remain active in the digestive system and/or will be more readily absorbed in an intact form.

Stably dimerized trefoil protein can be used in the methods of the invention. Such molecules can be prepared by stably crosslinking monomers of trefoil or by expressing a gene encoding a tandem repeat of a trefoil protein (e.g., ITF) or a portion thereof (e.g., a portion capable of forming the three loop structure characteristic of trefoil proteins).

Also useful in the method of the invention are trefoil proteins produced by chemical synthesis.

Trefoil proteins can be used to treat other disorders, e.g., Crohn's disease.

Trefoil proteins can be used to treat patients undergoing corneal transplants.

Other embodiments are within the following claims.

SEQUENCE LISTING

```
<160> NUMBER OF SEQ ID NOS: 21

<210> SEQ ID NO 1
<211> LENGTH: 431
<212> TYPE: DNA
<213> ORGANISM: Rattus norvegicus
<220> FEATURE:
<221> NAME/KEY: CDS
<222> LOCATION: (18)...(260)
```

-continued

```
<400> SEQUENCE: 1

gaagtttgcg tgctgcc atg gag acc aga gcc ttc tgg ata acc ctg ctg        50
                   Met Glu Thr Arg Ala Phe Trp Ile Thr Leu Leu
                    1               5                   10

ctg gtc ctg gtt gct ggg tcc tcc tgc aaa gcc cag gaa ttt gtt ggc       98
Leu Val Leu Val Ala Gly Ser Ser Cys Lys Ala Gln Glu Phe Val Gly
             15                  20                  25

cta tct cca agc caa tgt atg gcg cca aca aat gtc agg gtg gac tgt      146
Leu Ser Pro Ser Gln Cys Met Ala Pro Thr Asn Val Arg Val Asp Cys
         30                  35                  40

aac tac ccc act gtc aca tca gag cag tgt aac aac cgt ggt tgc tgt      194
Asn Tyr Pro Thr Val Thr Ser Glu Gln Cys Asn Asn Arg Gly Cys Cys
     45                  50                  55

ttt gac tcc agc atc cca aat gtg ccc tgg tgc ttc aaa cct ctg caa      242
Phe Asp Ser Ser Ile Pro Asn Val Pro Trp Cys Phe Lys Pro Leu Gln
 60                  65                  70                  75

gag aca gaa tgt aca ttt tgaagctgtc caggctccag gaagggagct             290
Glu Thr Glu Cys Thr Phe
                 80

ccacaccctg gactcttgct gatggtagtg gcccagggta acactcaccc ctgatctgct    350

ccctcgcgcc ggccaatata ggagctggga gtccagaaga ataaagacct tacagtcagc    410

acaaggctgt tctaattgcg g                                              431


<210> SEQ ID NO 2
<211> LENGTH: 81
<212> TYPE: PRT
<213> ORGANISM: Rattus norvegicus

<400> SEQUENCE: 2

Met Glu Thr Arg Ala Phe Trp Ile Thr Leu Leu Leu Val Leu Val Ala
 1               5                  10                  15

Gly Ser Ser Cys Lys Ala Gln Glu Phe Val Gly Leu Ser Pro Ser Gln
            20                  25                  30

Cys Met Ala Pro Thr Asn Val Arg Val Asp Cys Asn Tyr Pro Thr Val
        35                  40                  45

Thr Ser Glu Gln Cys Asn Asn Arg Gly Cys Cys Phe Asp Ser Ser Ile
    50                  55                  60

Pro Asn Val Pro Trp Cys Phe Lys Pro Leu Gln Glu Thr Glu Cys Thr
65                  70                  75                  80

Phe


<210> SEQ ID NO 3
<211> LENGTH: 400
<212> TYPE: DNA
<213> ORGANISM: Homo sapiens
<220> FEATURE:
<221> NAME/KEY: CDS
<222> LOCATION: (2)...(223)
<223> OTHER INFORMATION: Oligonucleotide for PCR

<400> SEQUENCE: 3

g atg ctg ggg ctg gtc ctg gcc ttg ctg tcc tcc agc tct gct gag gag     49
  Met Leu Gly Leu Val Leu Ala Leu Leu Ser Ser Ser Ser Ala Glu Glu
   1               5                  10                  15

tac gtg ggc ctg tct gca aac cag tgt gcc gtg ccg gcc aag gac agg       97
Tyr Val Gly Leu Ser Ala Asn Gln Cys Ala Val Pro Ala Lys Asp Arg
             20                  25                  30

gtg gac tgc ggc tac ccc cat gtc acc ccc aag gag tgc aac aac cgg      145
```

-continued

```
Val Asp Cys Gly Tyr Pro His Val Thr Pro Lys Glu Cys Asn Asn Arg
         35                  40                  45

ggc tgc tgc ttt gac tcc agg atc cct gga gtg cct tgg tgt ttc aag      193
Gly Cys Cys Phe Asp Ser Arg Ile Pro Gly Val Pro Trp Cys Phe Lys
     50                  55                  60

ccc ctg cag gaa gca gaa tgc acc ttc tga ggcacctcca gctgcccctg        243
Pro Leu Gln Glu Ala Glu Cys Thr Phe  *
 65                  70

ggatgcaggc tgagcaccct tgcccggctg tgattgctgc caggcactgt tcatctcagt    303

ttttctgtcc ctttgctccc ggcaagcttt ctgctgaaag ttcatatctg gagcctgatg    363

tcttaacgaa taaaggtccc atgctccacc cgaaaaa                             400


<210> SEQ ID NO 4
<211> LENGTH: 73
<212> TYPE: PRT
<213> ORGANISM: Homo sapiens

<400> SEQUENCE: 4

Met Leu Gly Leu Val Leu Ala Leu Leu Ser Ser Ser Ser Ala Glu Glu
 1               5                  10                  15

Tyr Val Gly Leu Ser Ala Asn Gln Cys Ala Val Pro Ala Lys Asp Arg
            20                  25                  30

Val Asp Cys Gly Tyr Pro His Val Thr Pro Lys Glu Cys Asn Asn Arg
        35                  40                  45

Gly Cys Cys Phe Asp Ser Arg Ile Pro Gly Val Pro Trp Cys Phe Lys
    50                  55                  60

Pro Leu Gln Glu Ala Glu Cys Thr Phe
65                  70


<210> SEQ ID NO 5
<211> LENGTH: 10
<212> TYPE: DNA
<213> ORGANISM: Artificial Sequence
<220> FEATURE:
<223> OTHER INFORMATION: Oligonucleotide for PCR

<400> SEQUENCE: 5

gggcggccgc                                                            10


<210> SEQ ID NO 6
<211> LENGTH: 21
<212> TYPE: DNA
<213> ORGANISM: Artificial Sequence
<220> FEATURE:
<223> OTHER INFORMATION: Oligonucleotide for PCR

<400> SEQUENCE: 6

gtacattctg tctcttgcag a                                               21


<210> SEQ ID NO 7
<211> LENGTH: 24
<212> TYPE: DNA
<213> ORGANISM: Artificial Sequence
<220> FEATURE:
<223> OTHER INFORMATION: Oligonucleotide for PCR

<400> SEQUENCE: 7

taaccctgct gctgctggtc ctgg                                            24


<210> SEQ ID NO 8
<211> LENGTH: 21
```

-continued

<212> TYPE: DNA
<213> ORGANISM: Artificial Sequence
<220> FEATURE:
<223> OTHER INFORMATION: Oligonucleotide for PCR

<400> SEQUENCE: 8 gtttgcgtgc tgccatggag a 21

<210> SEQ ID NO 9
<211> LENGTH: 21
<212> TYPE: DNA
<213> ORGANISM: Artificial Sequence
<220> FEATURE:
<223> OTHER INFORMATION: Oligonucleotide for PCR

<400> SEQUENCE: 9 ccgcaattag aacagccttg t 21

<210> SEQ ID NO 10
<211> LENGTH: 25
<212> TYPE: DNA
<213> ORGANISM: Artificial Sequence
<220> FEATURE:
<223> OTHER INFORMATION: Oligonucleotide for PCR

<400> SEQUENCE: 10 gcagtgtaac aaccgtggtt gctgc 25

<210> SEQ ID NO 11
<211> LENGTH: 60
<212> TYPE: PRT
<213> ORGANISM: Homo sapiens

<400> SEQUENCE: 11

Glu Ala Gln Thr Glu Thr Cys Thr Val Ala Pro Arg Glu Arg Gln Asn
1 5 10 15

Cys Gly Phe Pro Gly Val Thr Pro Ser Gln Cys Ala Asn Lys Gly Cys
20 25 30

Cys Phe Asp Asp Thr Val Arg Gly Val Pro Trp Cys Phe Tyr Pro Asn
35 40 45

Thr Ile Asp Val Pro Pro Glu Glu Glu Cys Glu Phe
50 55 60

<210> SEQ ID NO 12
<211> LENGTH: 62
<212> TYPE: PRT
<213> ORGANISM: Homo sapiens

<400> SEQUENCE: 12

Glu Lys Pro Ala Ala Cys Arg Cys Ser Arg Gln Asp Pro Lys Asn Arg
1 5 10 15

Val Asn Cys Gly Phe Pro Gly Ile Thr Ser Asp Gln Cys Phe Thr Ser
20 25 30

Gly Cys Cys Phe Asp Ser Gln Val Pro Gly Val Pro Trp Cys Phe Lys
35 40 45

Pro Leu Pro Ala Gln Glu Ser Glu Glu Cys Val Met Glu Val
50 55 60

<210> SEQ ID NO 13
<211> LENGTH: 318
<212> TYPE: DNA
<213> ORGANISM: Homo sapiens
<220> FEATURE:

-continued

```
<221> NAME/KEY: CDS
<222> LOCATION: (1)...(318)

<400> SEQUENCE: 13

gag aaa ccc tcc ccc tgc cag tgc tcc agg ctg agc ccc cat aac agg       48
Glu Lys Pro Ser Pro Cys Gln Cys Ser Arg Leu Ser Pro His Asn Arg
 1               5                  10                  15

acg aac tgc ggc ttc cct gga atc acc agt gac cag tgt ttt gac aat       96
Thr Asn Cys Gly Phe Pro Gly Ile Thr Ser Asp Gln Cys Phe Asp Asn
             20                  25                  30

gga tgc tgt ttc gac tcc agt gtc act ggg gtc ccc tgg tgt ttc cac      144
Gly Cys Cys Phe Asp Ser Ser Val Thr Gly Val Pro Trp Cys Phe His
         35                  40                  45

ccc ctc cca aag caa gag tcg gat cag tgc gtc atg gag gtc tca gac      192
Pro Leu Pro Lys Gln Glu Ser Asp Gln Cys Val Met Glu Val Ser Asp
     50                  55                  60

aga aga aac tgt ggc tac ccg ggc atc agc ccc gag gaa tgc gcc tct      240
Arg Arg Asn Cys Gly Tyr Pro Gly Ile Ser Pro Glu Glu Cys Ala Ser
 65                  70                  75                  80

cgg aag tgc tgc ttc tcc aac ttc atc ttt gaa gtg ccc tgg tgc ttc      288
Arg Lys Cys Cys Phe Ser Asn Phe Ile Phe Glu Val Pro Trp Cys Phe
                 85                  90                  95

ttc ccg aac tct gtg gaa gac tgc cat tac                              318
Phe Pro Asn Ser Val Glu Asp Cys His Tyr
            100                 105


<210> SEQ ID NO 14
<211> LENGTH: 105
<212> TYPE: PRT
<213> ORGANISM: Homo sapiens

<400> SEQUENCE: 14

Lys Pro Ser Pro Cys Gln Cys Ser Arg Leu Ser Pro His Asn Arg Thr
 1               5                  10                  15

Asn Cys Gly Phe Pro Gly Ile Thr Ser Asp Gln Cys Phe Asp Asn Gly
            20                  25                  30

Cys Cys Phe Asp Ser Ser Val Thr Gly Val Pro Trp Cys Phe His Pro
        35                  40                  45

Leu Pro Lys Gln Glu Ser Asp Gln Cys Val Met Glu Val Ser Asp Arg
    50                  55                  60

Arg Asn Cys Gly Tyr Pro Gly Ile Ser Pro Glu Glu Cys Ala Ser Arg
65                  70                  75                  80

Lys Cys Cys Phe Ser Asn Phe Ile Phe Glu Val Pro Trp Cys Phe Phe
                85                  90                  95

Pro Asn Ser Val Glu Asp Cys His Tyr
            100                 105


<210> SEQ ID NO 15
<211> LENGTH: 540
<212> TYPE: DNA
<213> ORGANISM: Homo sapiens
<220> FEATURE:
<221> NAME/KEY: CDS
<222> LOCATION: (41)...(292)
<223> OTHER INFORMATION:

<400> SEQUENCE: 15

atccctgact cggggtcgcc tttggagcag agaggaggca atg gcc acc atg gag       55
                                            Met Ala Thr Met Glu
                                             1               5

aac aag gtg atc tgc gcc ctg gtc ctg gtg tcc atg ctg gcc ctc ggc      103
```

-continued

```
Asn Lys Val Ile Cys Ala Leu Val Leu Val Ser Met Leu Ala Leu Gly
                10                  15                  20

acc ctg gcc gag gcc cag aca gag acg tgt aca gtg gcc ccc cgt gaa      151
Thr Leu Ala Glu Ala Gln Thr Glu Thr Cys Thr Val Ala Pro Arg Glu
            25                  30                  35

aga cag aat tgt ggt ttt cct ggt gtc acg ccc tcc cag tgt gca aat      199
Arg Gln Asn Cys Gly Phe Pro Gly Val Thr Pro Ser Gln Cys Ala Asn
        40                  45                  50

aag ggc tgc tgt ttc gac gac acc gtt cgt ggg gtc ccc tgg tgc ttc      247
Lys Gly Cys Cys Phe Asp Asp Thr Val Arg Gly Val Pro Trp Cys Phe
    55                  60                  65

tat cct aat acc atc gac gtc cct cca gaa gag gag tgt gaa ttt          292
Tyr Pro Asn Thr Ile Asp Val Pro Pro Glu Glu Glu Cys Glu Phe
70                  75                  80

tagacacttc tgcagggatc tgcctgcatc ctgacggggt gccgtcccca gcacggtgat    352

tagtcccaga gctcggctgc cacctccacc ggacacctca gacacgcttc tgcagctgtg    412

cctcggctca caacacagat tgactgctct gactttgact actcaaaatt ggcctaaaaa    472

ttaaaagaga tcgatattaa aaaaaaaaaa aaaaaaaaaa aaaaaaaaaa aaaaaaaaaa    532

aaaaaaaa                                                             540


<210> SEQ ID NO 16
<211> LENGTH: 84
<212> TYPE: PRT
<213> ORGANISM: Homo sapiens

<400> SEQUENCE: 16

Met Ala Thr Met Glu Asn Lys Val Ile Cys Ala Leu Val Leu Val Ser
1               5                   10                  15

Met Leu Ala Leu Gly Thr Leu Ala Glu Ala Gln Thr Glu Thr Cys Thr
            20                  25                  30

Val Ala Pro Arg Glu Arg Gln Asn Cys Gly Phe Pro Gly Val Thr Pro
        35                  40                  45

Ser Gln Cys Ala Asn Lys Gly Cys Cys Phe Asp Asp Thr Val Arg Gly
    50                  55                  60

Val Pro Trp Cys Phe Tyr Pro Asn Thr Ile Asp Val Pro Pro Glu Glu
65                  70                  75                  80

Glu Cys Glu Phe


<210> SEQ ID NO 17
<211> LENGTH: 23
<212> TYPE: DNA
<213> ORGANISM: Artificial Sequence
<220> FEATURE:
<223> OTHER INFORMATION: Oligonucleotide for PCR

<400> SEQUENCE: 17

tgaccctgtg tcatcaccct ggc                                             23


<210> SEQ ID NO 18
<211> LENGTH: 20
<212> TYPE: DNA
<213> ORGANISM: Artificial Sequence
<220> FEATURE:
<223> OTHER INFORMATION: Oligonucleotide for PCR

<400> SEQUENCE: 18

cggctgctct gatggccgcc                                                 20
```

-continued

```
<210> SEQ ID NO 19
<211> LENGTH: 21
<212> TYPE: DNA
<213> ORGANISM: Artificial Sequence
<220> FEATURE:
<223> OTHER INFORMATION: Oligonucleotide for PCR

<400> SEQUENCE: 19

gccggccaca gtcgatgaat c                                          21


<210> SEQ ID NO 20
<211> LENGTH: 23
<212> TYPE: DNA
<213> ORGANISM: Artificial Sequence
<220> FEATURE:
<223> OTHER INFORMATION: Oligonucleotide for PCR

<400> SEQUENCE: 20

gagaggttgc tgttttgatg aca                                        23


<210> SEQ ID NO 21
<211> LENGTH: 23
<212> TYPE: DNA
<213> ORGANISM: Artificial Sequence
<220> FEATURE:
<223> OTHER INFORMATION: Oligonucleotide for PCR

<400> SEQUENCE: 21

gccaagtctt gatgtagcca gtt                                        23
```

What is claimed is:

[1. A method for the treatment of a disruption of the corneal epithelium in a pateint, said method comprising administering to the eye of said patient a trefoil protein selected from the group consisting of intestinal trefoil factor (ITF), spasmolytic peptide (SP), pS2, and biologically active fragments thereof.]

[2. The method of claim 1, wherein said trefoil protein is a human trefoil protein.]

[3. The method of claim 2, wherein said trefoil protein is intestinal trefoil factor (ITF).]

[4. The method of claim 2, wherein said trefoil protein is spasmolytic peptide (SP).]

[5. The method of claim 2, wherein said trefoil protein is pS2.]

[6. The method of claim 1, wherein said disorder is a corneal ulcer, or is caused by a traumatic physical injury, eye surgery, a chemical exposure, or an ultraviolet light exposure.]

[7. The method of claim 1, wherein administration is topical.]

*8. A method for the treatment of a disruption of the corneal epithelium in a patient, said method comprising administering to the eye of said patient a trefoil protein comprising a region having at least 90% sequence identity to residues 33–70 of the polypeptide set forth in SEQ ID NO: 2, or at least 90% sequence identity to residues 25–62 of the polypeptide set forth in SEQ ID NO: 4, wherein said trefoil protein has the ability to enhance corneal epithelial wound healing.*

*9. The method of claim 8, wherein said trefoil protein is the polypeptide set forth in SEQ ID NO: 2 or a biologically active fragment thereof comprising residues 33–70 of said polypeptide set forth in SEQ ID NO: 2, wherein said trefoil protein has the ability to enhance corneal epithelial wound healing.*

*10. The method of claim 8, wherein said trefoil protein is the polypeptide set forth in SEQ ID NO: 4 or a biologically active fragment thereof comprising residues 25–62 of said polypeptide set forth in SEQ ID NO: 4, wherein said trefoil protein has the ability to enhance corneal epithelial wound healing.*

*11. The method of claim 8, wherein said trefoil protein comprises a region having at least 90% sequence identity to residues 33–70 of the polypeptide set forth in SEQ ID NO: 2, wherein said trefoil protein has the ability to enhance corneal epithelial wound healing.*

*12. The method of claim 8, wherein said trefoil protein comprises a region having at least 90% sequence identity to residues 25–62 of the polypeptide set forth in SEQ ID NO: 4, wherein said trefoil protein has the ability to enhance corneal epithelial wound healing.*

*13. The method of claim 8, wherein said disruption is a corneal ulcer, or is caused by a traumatic physical injury, eye surgery, a chemical exposure, or an ultraviolet light exposure.*

*14. The method of claim 8, wherein administration is topical.*

*15. A method for the treatment of a disruption of the corneal epithelium in a patient, said method comprising administering to the eye of said patient a trefoil protein comprising a region having at least 90% sequence identity, over more than 35 contiguous amino acid residues, to the polypeptide set forth in SEQ ID NO: 2 or 4, wherein said trefoil protein has the ability to enhance corneal epithelial wound healing.*

*16. The method of claim 15, wherein said trefoil protein is the polypeptide set forth in SEQ ID NO: 2 or a biologically active fragment thereof comprising more than 35 contiguous amino acid residues of the polypeptide set forth in SEQ ID NO: 2, wherein said trefoil protein has the ability to enhance corneal epithelial wound healing.*

*17. The method of claim 15, wherein said trefoil protein is the polypeptide set forth in SEQ ID NO: 4 or a biologically active fragment thereof comprising more than 35 contiguous amino acid residues of the polypeptide set forth in SEQ ID NO: 4, wherein said trefoil protein has the ability to enhance corneal epithelial wound healing.*

*18. The method of claim 15, wherein said trefoil protein comprises a region having at least 90% sequence identity, over more than 35 contiguous amino acid residues, to the polypeptide set forth in SEQ ID NO: 2, wherein said trefoil protein has the ability to enhance corneal epithelial wound healing.*

*19. The method of claim 15, wherein said trefoil protein comprises a region having at least 90% sequence identity, over more than 35 contiguous amino acid residues, to the polypeptide set forth in SEQ ID NO: 4, wherein said trefoil protein has the ability to enhance corneal epithelial wound healing.*

*20. The method of claim 15, wherein said disruption is a corneal ulcer, or is caused by a traumatic physical injury, eye surgery, a chemical exposure, or an ultraviolet light exposure.*

*21. The method of claim 15, wherein administration is topical.*

* * * * *

UNITED STATES PATENT AND TRADEMARK OFFICE

CERTIFICATE OF CORRECTION

PATENT NO. : RE 41,028 E
APPLICATION NO. : 10/457157
DATED : December 1, 2009
INVENTOR(S) : Podolsky It is certified that error appears in the above-identified patent and that said Letters Patent is hereby corrected as shown below:

Title Page;
Cover Sheet, replace Item (54) (Title) with --TREATING EYE DISORDERS USING INTESTINAL TREFOIL PROTEINS--;

Cover Sheet, replace Item (63) with --Reissue of U.S. application Ser. No. 09/313,434, filed May 17, 1999, issued as U.S. Pat. No. 6,525,018, which is a continuation-in-part of U.S. application Ser. No. 10/362,310, filed Feb. 19, 2003, which is the National Stage of International Application No. PCT/US97/06004, filed Apr. 11, 1997, which was published in English under PCT Article 21 (2), and which is a continuation-in-part of U.S. application Ser. No. 08/631,469, filed Apr. 12, 1996, issued as U.S. Pat. No. 6,221,840.--;

Items (56)
Cover Sheet, Under OTHER PUBLICATIONS, in Bare et al., replace "877-879" with --872-879--;

Cover Sheet, Under OTHER PUBLICATIONS, replace "Wbsters Dictionary-definition trefoil, 1998" with --Webster's Dictionary-definition trefoil, 1998--; and Cover Sheet, Under OTHER PUBLICATIONS, replace "Blast alignment of human and rat ITF, currently know as" with --Blast alignment of human and rat ITF, currently known as--.

Page 2, Under OTHER PUBLICATIONS, in Hauser et al. replace "hP1.B5" with --hP1.B,--;

Signed and Sealed this

Thirtieth Day of November, 2010

David J. Kappos

David J. Kappos
*Director of the United States Patent and Trademark Office*

Items (56)

Page 2, Under OTHER PUBLICATIONS, in Falk et al., replace "α-1/ ,3/4-Fucosyltransferase" with --α-1, 3/4-Fucosyltransferase--;

In Falk et al., replace "He licobacter" with --Helicobacter--;

In Jakowlew et al., replace "breast cell" with --breast cancer cell--;

In Jakowlew et al., replace "1994" with --1984--;

In Beers, replace "diagnostic" with --diagnosis--;

In Beers, replace "seventh" with --seventeenth--;

In Byrne et al., replace "DDS" with --DSS--;

In Byrne et al., replace "CD4*CD45RB$^{RI}$T cell" with --CD4$^{+}$CD45RB$^{Hi}$ T cell--; and In Chinery et al., replace "damage in rat" with --damage in the rat--.

Page 3, Under OTHER PUBLICATIONS, in Fleiszig et al., replace "*Pseudomones*" with --*Pseudomonas*--;

In Hammer et al., replace "*Gasteroenterologische*" with --*Gastroenterologische*--;

Page 3, Under OTHER PUBLICATIONS, in Hoffmann et al., replace "*Histropathology*" with --*Histopathology*--;

In Iwakiri et al., replace "silence" with --silencer--;

In Iwakiri et al., replace "*Gasterology*" with --*Gastroenterology*--;

In Ngo et al., replace "*Tertlary*" with --*Tertiary*--; and

In On-Line Medical Dictionary; definition of mucostis, replace "mucostis" with --mucositis--.

Page 4, Under OTHER PUBLICATIONS, in Segars et al., replace "aminosalicytic" with --aminosalicylic--, In Stein et al., replace "et asl." with --et al.--;

In Taupin et al., replace "kinase regulates" with --kinase activation regulates--;

In Taupin et al., replace "differentation" with --differentiation--;

In Tebbutt et al., replace "homostatis" with --homeostasis--;

In Thim et al., replace "Plasma" with --plasma--; and

Page 4, Under OTHER PUBLICATIONS, In Jagla et al., replace "530." with --530 (1999).--.

Column 1, Lines 1-2, replace "TREATING EYE DISORDERS INTESTINAL TREFOIL PROTEINS" with --TREATING EYE DISORDERS USING INTESTINAL TREFOIL PROTEINS--.

Column 2, Line 16, replace "diseaase" with --disease--.

Column 5, Lines 19-20, replace "GCC" with --GCG--.

Column 8, Line 26, replace "unclear," with --unclear;--; and

Line 27, replace "mutation" with --mutational--.

Column 10, Line 25, replace "neutrophenia" with --neutropenia--;

Line 28, replace "rITf" with --rITF--;

Line 43, replace "form" with --from--; and

Line 67, replace "FIG. 2; SEQ ID.:2" with --FIG. 2; SEQ ID NO. :2--.

Column 11, Line 8, replace "rITf" with --rITF--.

Column 12, Line 8, replace "E. coli DNa" with --*E.coli* DNA--;

Line 18, replace "Lmabda" with --Lambda--;

Line 41, replace "encodes" with --encode--;

Line 43, replace "hITf" with --hITF--;

Line 63, replace "cDNa" with --cDNA--; and

Line 63, replace "hITf" with --hITF--.

Column 13, Line 1, replace "rITf" with --rITF--; and

Line 56, replace "scrappings" with --scrapings--.

Column 14, Line 32, replace “cDNa” with --cDNA--;

Line 41, replace “hITf” with --hITF--; and

Line 51, replace “drosphilia” with --drosophila--.

Column 15, Line 8, replace “hITf” with --hITF--;

Line 22, replace “hITf” with --hITF--;

Line 51, replace “selecting the neo” with --selecting for neo--; and

Line 58, replace “Li et al., 1991” with --Li et al., 1992--.

Column 16, Line 20, replace “repeated 30 times;” with --repeated 30 times:--;

Line 41, replace “Jeffrey et al., 1984” with --Jeffrey et al., 1994--;

Line 45, replace “oligonucletoide” with --oligonucleotide--;

Line 50, replace “GenAmp” with --GeneAmp--; and

Line 65, replace “order” with --other--.

Column 17, Line 40, replace “animal’s” with --animals’--.

Column 18, Line 14, replace “tip within the five days” with --tip within five days--;

Line 19, replace “Poulson” with --Poulsom--;

Line 37, replace “methotraxate” with --methotrexate--; and

Line 58, replace “method” with --model--.

Column 19, Line 16, replace “aproptinin” with --aprotinin--;

Line 29, replace “concetration” with --concentration--; and

Line 31, replace “methanol-mixed” with --methanol-fixed--.

Column 20, Line 18, replace “Reactor” with --Receptor--.

Column 21, Line 47, replace “Nikon Diphaor” with --Nikon Diaphor--; and

Line 61, replace “100 mg/ml” with --100 ng/ml--.

Column 22, Line 4, replace “promotion” with --promoting--;

Line 32, replace “p=0.002” with --p=0.0002--;

Line 39, replace “Steibel” with --Stiebel--; and

Line 51, replace “Cornal” with --Corneal--.

Column 23, Line 28, replace “corneal epithelium” with --corneal central epithelium--; and Line 36, replace “occular” with --ocular--.

Column 24, Line 6, replace “requirements” with --regimens--;

Line 14, replace “pateint” with --patient--; and

Line 25, replace “intestinal or blood serum” with --intestinal tissue or blood serum--.

Column 35, Line 35, replace “pateint” with --patient--.